US008209128B1

(12) United States Patent
Gourley

(10) Patent No.: US 8,209,128 B1
(45) Date of Patent: Jun. 26, 2012

(54) NANOLASER SPECTROSCOPY AND MICRO-OPTICAL RESONATORS FOR DETECTING, ANALYZING, AND MANIPULATING BIOPARTICLES

(75) Inventor: Paul L. Gourley, Albuquerque, NM (US)

(73) Assignee: Paul L. Gourley, Albuquerque, NM (US)

( * ) Notice: Subject to any disclaimer, the term of this patent is extended or adjusted under 35 U.S.C. 154(b) by 730 days.

(21) Appl. No.: 12/034,640

(22) Filed: Feb. 20, 2008

Related U.S. Application Data

(60) Provisional application No. 60/902,685, filed on Feb. 21, 2007.

(51) Int. Cl.
*G01N 33/48* (2006.01)
(52) U.S. Cl. .......... 702/19; 436/172; 356/318; 356/338; 356/339; 356/417
(58) Field of Classification Search .................... 702/19; 436/522, 524, 526, 171, 172, 164, 94, 57; 356/246, 318, 338, 339, 417, 471; 250/461.2, 250/458.1, 459.1; 210/634; 372/45.01, 92, 372/108, 26, 39; 324/765, 753
See application file for complete search history.

(56) References Cited

U.S. PATENT DOCUMENTS

| | | | |
|---|---|---|---|
| 5,596,401 A * | 1/1997 | Kusuzawa | 356/23 |
| 5,608,519 A | 3/1997 | Gourley | |
| 5,793,485 A * | 8/1998 | Gourley | 356/318 |
| 5,920,390 A * | 7/1999 | Farahi et al. | 356/477 |
| 6,187,592 B1 | 2/2001 | Gourley | |
| 6,454,945 B1 * | 9/2002 | Weigl et al. | 210/634 |
| 6,668,111 B2 | 12/2003 | Tapalain | |
| 6,833,542 B2 | 12/2004 | Wang | |
| 6,884,624 B1 | 4/2005 | Gourley | |
| 6,975,400 B2 | 12/2005 | Ortyn | |
| 6,999,170 B2 | 2/2006 | Takeuchi | |
| 7,050,613 B2 | 5/2006 | Murao | |
| 7,095,010 B2 | 8/2006 | Scherer | |
| 7,122,384 B2 * | 10/2006 | Prober et al. | 436/524 |
| 7,149,396 B2 | 12/2006 | Schmidt | |
| 7,149,561 B2 | 12/2006 | Diab | |

(Continued)

FOREIGN PATENT DOCUMENTS

JP 2002019268 A * 1/2002

(Continued)

OTHER PUBLICATIONS

Gourley, "Biocavity Laser for High-Speed Cell and Tumor Biology," J. Phys. D: Appl. Phys. 36 (14) R228-R239 (2003).

(Continued)

*Primary Examiner* — Carol Tsai

(57) ABSTRACT

This invention provides a new method for rapidly analyzing single bioparticles to assess their material condition and state of health. The method is enabled by use of a resonant cavity apparatus to measure an optical property related to the bioparticle size and refractive index. Measuring the refractive index is useful for determining material properties of the bioparticle. The material properties depend on the biomolecular composition of the bioparticle. The biomolecular composition is, in turn, dependent on the state of health of the bioparticle. Thus, measured optical properties can be used to differentiate normal (healthy) and abnormal (diseased) states of bioparticles derived from cells or tissues. The method is illustrated with data obtained from a resonator with a gain medium. The invention also provides new methods for making multiple measurements in a single device and detecting, analyzing, and manipulating bioparticles that are much smaller than the wavelength of light.

11 Claims, 13 Drawing Sheets

U.S. PATENT DOCUMENTS

| | | | |
|---|---|---|---|
| 7,187,441 | B1 | 3/2007 | Sevick-Muraca |
| 7,257,279 | B2 * | 8/2007 | Guo et al. .................. 385/12 |
| 7,279,883 | B2 | 10/2007 | Sohn |
| 7,294,503 | B2 | 11/2007 | Quake |
| 7,298,478 | B2 | 11/2007 | Gilbert |
| 7,393,699 | B2 * | 7/2008 | Tran ................................ 438/1 |
| 7,573,921 | B2 * | 8/2009 | Yumoto et al. .................. 372/22 |
| 7,733,497 | B2 * | 6/2010 | Yun et al. ....................... 356/497 |
| 2005/0118731 | A1 * | 6/2005 | Salafsky ...................... 436/518 |
| 2005/0201425 | A1 * | 9/2005 | Yakymyshyn et al. ......... 372/12 |
| 2007/0269901 | A1 * | 11/2007 | Armani et al. ................ 436/172 |
| 2007/0285843 | A1 * | 12/2007 | Tran .......................... 360/245.9 |
| 2008/0181828 | A1 * | 7/2008 | Kluck ........................... 422/128 |
| 2009/0214755 | A1 * | 8/2009 | Armani et al. ............... 427/2.13 |

FOREIGN PATENT DOCUMENTS

JP        2005091467 A  *  4/2005

OTHER PUBLICATIONS

Gourley et al., "Semiconductor Microcavity Laser Spectroscopy . . . ," SPIE Conf. pub. 4265, Photonics West 4265, 113-125 (2001).

Gourley, et al. "Nano-squeezed light . . . ," SPIE Conf. pub 5345, Photonics West, Jan. 26-27, 2004, San Jose, CA, p. 51-60.

Gourley, et al., "Biomolecular Divergence . . . ," J. BioMedical Optics 12, p. 054003-1 to 14, (2007).

Gourley, et al., "Biocavity Laser Spectroscopy . . . ," SPIE Conf, San Jose, CA, Jan. 23-25, 2006.

Gourley, et al., "Optical Phenotyping . . . ," IEEE J. of Selected Topics in Quantum Electron. 11, Jul./Aug. 2005, p. 818-826.

Gourley, et al. "Brief Overview of BioMicroNano Technologies," Biotechnololgy Progress 21, 2-10 (2005).

Beauvoit, T. Kitai, and B. Chance, "Contribution of the mitochondrial compartment to the optical properties of the rat liver: a theoretical and practical approach.," Biophys J. 67(6), 2501-2510. (1994).

Karu, T. I., L. V. Pyatibrat, S. F. Kolyakov, N. I. Afanasyeva, "Absorption measurements of a cell monolayer relevant to phototherapy: Reduction of cytochrome c oxidase under near IR radiation," Journal of Photochemistry and Photobiology B: Biology 81, 98-106 (2005).

Barer, R. "Refractometry and Interferometry of Living Cells," J. Opt. Soc. Am. 47, pp. 545-552. (1957).

Landau, L. D. and E. M. Lifshitz, Statistical Physics, 2 ed. (Pergamon Press, New York, 1970), pp. 277-279.

Lindgren, B., Statistical Theory, 4th ed. (Chapman and Hall/CRC, Boca Raton, 1993).

Born, M. and E. Wolf, Principles of Optics, (Pergamon, Oxford, 1980), chapter 7.

* cited by examiner

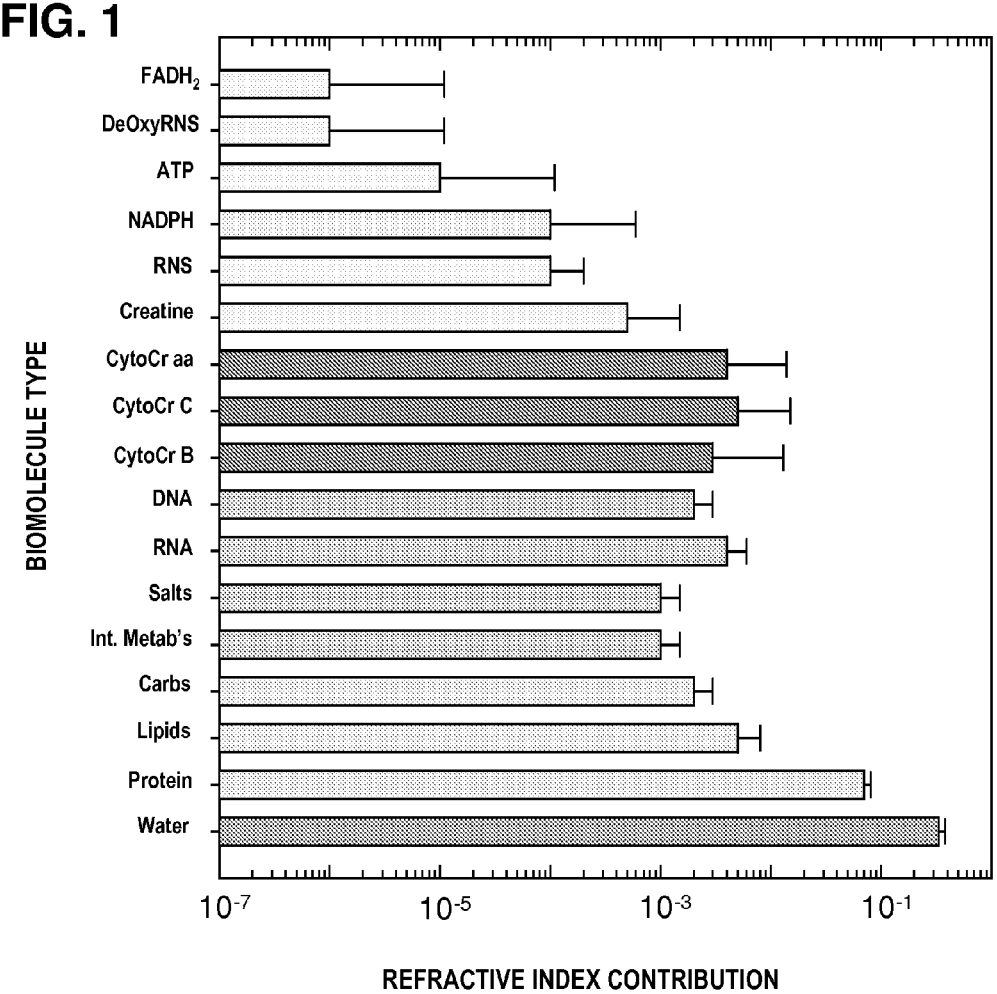

TOP VIEW

ΔL

L

SIDE VIEW

56 GRADED CAVITY

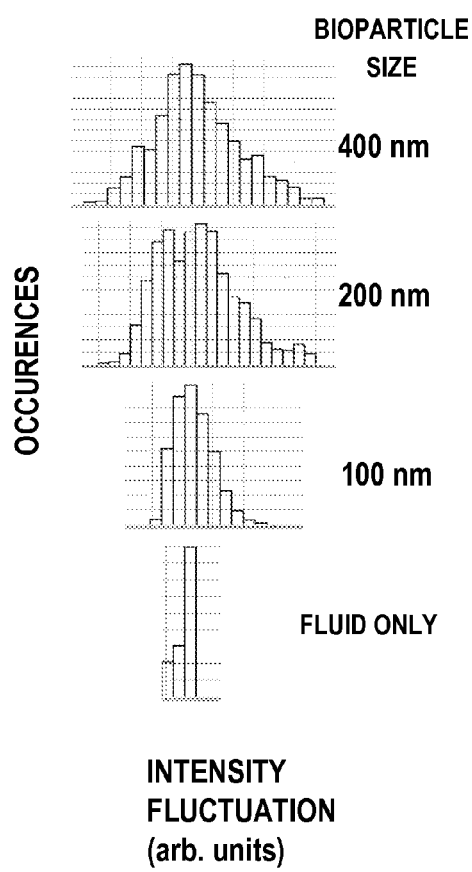
FIG. 11a
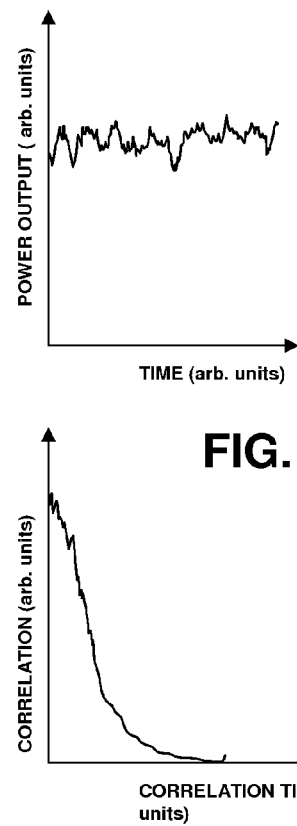
FIG. 11b
FIG. 11c

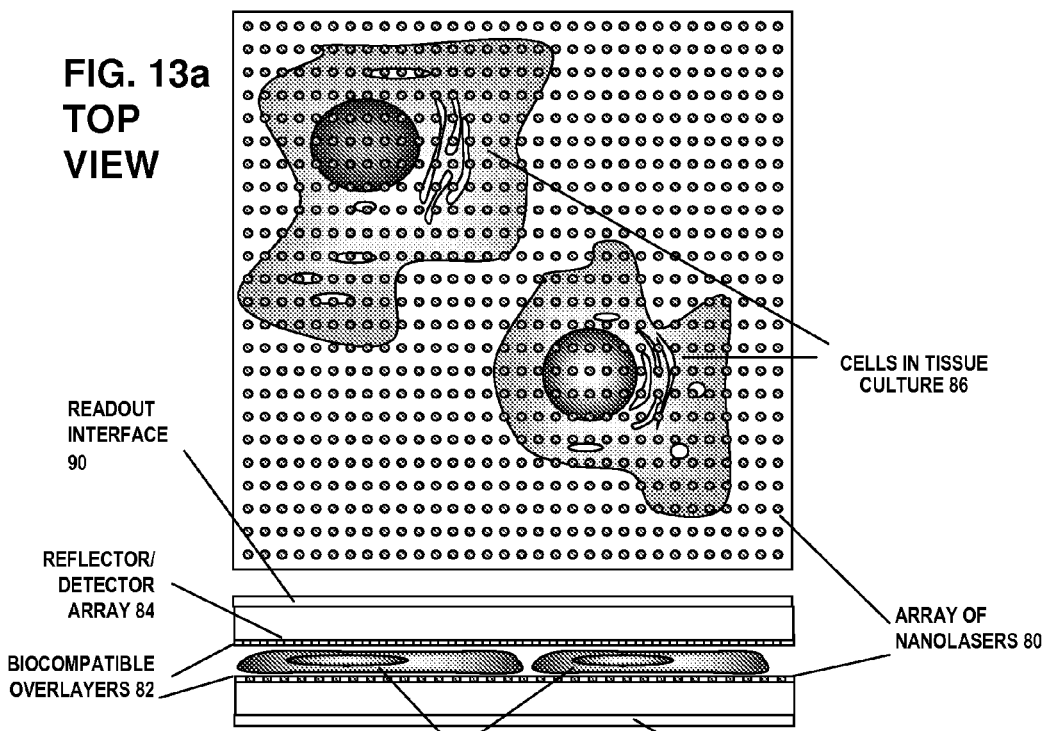

NANOLASER SPECTROSCOPY AND MICRO-OPTICAL RESONATORS FOR DETECTING, ANALYZING, AND MANIPULATING BIOPARTICLES

This application claims priority benefit from U.S. Provisional Patent Application Ser. No. 60/902,685, filed on Feb. 21, 2007, which is incorporated herein by reference.

The United States Government has rights in this invention through a Department of Energy agreement with the inventor.

SUMMARY

Using a nanoscale semiconductor laser, this invention provides a method for rapidly distinguishing between diseased and normal cells. Moreover, this new technique has the potential of detecting cancer at a very early stage, a development that could change profoundly the way cancer is diagnosed and treated. To investigate tumors, pathologists currently rely on labor-intensive microscopic examination, using older cell-staining methods that can be time-consuming and may give false readings. BioMEMs, biosensors, microcavity optical resonators, and nanolaser devices are powerful new tools for the rapid, accurate analysis of optical properties of cells, organelles, and other bioparticles. The optical properties of bioparticles depend upon their geometry and biomolecular composition. The invention described here provides methods to relate measured optical properties to bioparticle size and refractive index. In turn, the invention shows how to relate the refractive index to the overall biomolecular composition. And, it shows how to quantify the way in which dominant and other biomolecules contribute to the refractive index. It reveals how the index changes with alterations in the distribution of biomolecules. The invention also provides methods for calibrating and maintaining the fidelity of measurements during operation of devices.

The invention also describes methods for analyzing bioparticles using resonant cavity devices to determining statistical properties of an optical parameter called $\Delta\lambda$ that is related to the biomolecular composition of the particles. This enables a powerful analytical tool for studying disease, in general, in cells and organelles. Unlike any other single chemical or biophysical measurement, $\Delta\lambda$ is a measure of the overall biophysical state of the cell and organelles. The biophysical state of a cell is a reflection of its sum total of changes in biomolecular composition and organization. These properties can be used to differentiate normal and abnormal states of the particles by measuring distributions of optical properties among a population. It can also be used to identify healthy and diseased or stressed states of bioparticles derived from living cells or tissues.

The invention also provides a simple apparatus for multiple measurements, including size, morphology, and refractive index, in a single device. And, the invention provides a new method for detecting and measuring physical properties of very small bioparticles using light fluctuations arising from the interaction of bioparticles with resonant light waves within a resonant cavity. Further, the invention provides a new method for the simultaneous detection, analysis, and separation of small bioparticles using optical microcavities or nanolasers.

By using these methods with such devices to detect and analyze intrinsic optical properties of biological specimens, considerable advantages are gained. One important advantage is that no fluorescent probes are needed so specimens can be analyzed in seconds to minutes with no special preparation for rapid front-end screening of specimen biophysical properties. The description of the analysis and apparatus here focuses on biomedical applications, but the present invention is not limited to biomedical and has application to other kinds of organic and inorganic particles as well.

FIELD OF THE INVENTION

This invention relates to methods of analyzing data from biological micro-electromechanical systems (bioMEMs). The analysis method has application to microsystems biosensor, optical resonator, and micro- and nanolaser devices that measure optical properties of biological cells, organelles, bioparticles, and molecules.

BACKGROUND OF THE INVENTION

BioMEMs technologies derive from novel developments in materials and micro/nanofabrication methods. The prior art cited teaches how to use these integrated technologies (e.g., microfluidics, electronics and photonics, and biocompatible surface chemistries) to create fluidic systems that are well-suited to carry, manipulate, detect, analyze and process biological molecules, organelles, and whole cells. These systems also benefit from new light sources derived from semiconductors and solid state devices to enable efficient new tools for bioanalysis because they are small, easily integrated with microfluidics, and are well-adapted to microscopy and spectroscopy for imaging, flow spectrocytometry, and high speed analysis.

This invention teaches methods for analyzing data from resonant optical devices used to measure molecules, organelles, and cells (collectively called bioparticles here). Measurements of any optical property of a bioparticle from other device also benefits from this analysis. The an optical property called $\Delta\lambda$ that represents the difference between a measured resonance wavelength of a bioparticle in an optical cavity and a reference wavelength. The discussion can be generalized to other optical measurements from a biosensor.

The invention uses optical resonators to measure biophysical properties of bioparticles. The optical resonator can take many different forms by using different materials, geometries, wavelength regions, surface treatments or means for coupling light into or out of the resonator.

Generally, the resonator is a reflective structure comprising a cavity space for fluidic specimens. It comprises a means for internal or external light generation and a means for coupling light into and out of the structure. It allows the establishment of a resonance of light waves within the cavity and means to measure the resonance condition in the absence or presence of a specimen. The resonator may be constructed with materials such as dielectrics, metals, glasses, plastics, semiconductors, polymers or the like. The structure may take on different geometrical forms such as planar, box-like, rod, cylindrical, ring, spherical, or more complex shapes. It includes structures like waveguides, photonic lattices, periodic bandgap materials, or holey fibers. The geometry may include nanostructured components like quantum dots, arrays, wires, or layers. It may comprise surface treatments such as coatings, chemically functionalized surfaces, layers, processing, or thermal treatments to enhance the cavity optical performance or facilitate fluidic transport of specimens into and out of the cavity. In the discussion to follow, a planar mirror cavity forming a laser is used to illustrate the operation and method of analyzing bioparticles. However, the invention is not limited to a laser or limited by these choices of material and geometry.

In prior art, a biocavity laser device was developed for the analysis of cells. It relies on recent semiconductor micro/nanotechnology that has reduced the size of a laser to ultra small dimensions (tens of nanometers to microns) that match the size of bioparticles. The laser was integrated with a microfluidic chip to flow and analyze populations of bioparticles. It has shown the potential to probe the human immune system, characterize genetic disorders, and distinguish cancerous from normal cells. Most importantly, cells can be analyzed immediately after they are removed from the body. There are no time delays or difficulties associated with chemical fixing or tagging cells with stains or fluorescent markers. The applications of such a portable biological sensing device are potentially far-reaching, including realtime biopsy to enable surgeons and their patient's confidence that all of the diseased tissue had been removed during surgery.

The laser has recently been extended to the analysis of small bioparticles (smaller than the wavelength of light) such as organelles using a phenomenon called "nano-squeezed light." The laser light is "nano-squeezed" through the organelle and a single lasing mode is supported. This results in a discrete band of laser light with a simpler spectrum to analyze compared to whole cells.

The laser works on the principle that the speed of light through a biological cell is slowed by the presence of biomolecules. By flowing a fluid, cells, or bioparticles through a semiconductor microcavity laser, these decreases in light speed can be registered as small wavelength red-shifts in the emitted laser output spectrum. The biocavity laser is used to measure this biophysical optic parameter $\Delta\lambda$, a laser wavelength shift relating to the optical density of cell or organelles that reflects its size and biomolecular composition. As such, $\Delta\lambda$ is a powerful parameter that rapidly interrogates the biomolecular state of single cells and organelles. The laser shift $\Delta\lambda$ can be viewed as a wavelength detuning (or alternately as a frequency detuning $\Delta\omega$) of the cavity resonance in dimensionless units as $\delta=\Delta\lambda/\lambda=\Delta\omega/\omega$ where $\lambda$ and $\omega$ are the fluid-filled cavity (without cell) resonance wavelength and frequency, respectively. Experimentally, $\Delta\lambda$ is measured in nanometers as the difference between a longitudinal laser mode of the fluid-filled cavity and the red-shifted laser wavelength produced by flowing cells or organelles (e.g. mitochondria) through the cavity.

Because of its importance, it is essential to properly interpret the measurement and make highly accurate measurements of $\Delta\lambda$. This invention improves upon the interpretation and accuracy of measuring $\Delta\lambda$ in the following ways:

1. It provides a means for interpreting the measurement. The invention solves a technical difficulty in knowing exactly how the wavelength shift $\Delta\lambda$ relates to the biophysical properties (i.e. the diameter and refractive index) of the particle. Basically, the problem centers on determining the resonance frequencies of a particle in a planar active cavity with optical gain. The problem is not exactly solvable, but recent experiments on a variety of particles in various cavities have shown that a good approximation is given by a simple empirical relationship $$\Delta\lambda = kd\Delta n \quad (1)$$

where $\Delta n$ is the difference in refractive index between the particle and its surrounding fluid, d is the average particle diameter, and k is a constant relating to the geometry of the cavity. These results are an improvement over prior art that lead to inaccuracies in determining biophysical parameters.

2. It provides a means for predicting the distribution of $\Delta\lambda$ among a population. Using the empirical relationship in Eq. 1, it is possible to develop statistical methods to predict how the probability distribution of $\Delta\lambda$ should depend on the biophysical quantities d and $\Delta n$. Experiments show that the probability distribution of diameters for a given type of bioparticle is very often approximated by a normal distribution function. This is not necessarily the case for the probability distribution of $\Delta n$.

3. It provides a means for improving the accuracy of the measurement of $\Delta\lambda$. The invention solves another technical difficulty relating to errors in the measurement of $\Delta\lambda$. $\Delta\lambda$ depends on the accurate measure of both the lasing mode wavelength the reference wavelength. Because of possible instrumental drift effects, the bioparticle resonance wavelength and/or reference wavelength may change with time and cause errors in the computation of $\Delta\lambda$. It is important to provide a means to correct for this drift to allow accurate computation of $\Delta\lambda$.

4. It provides a means for absolute calibration of the measurement of $\Delta\lambda$. The measurement of the $\Delta\lambda$ can sometimes be complicated by the calibration of the zero of measurement. Knowing the relationship between the measured property $\Delta\lambda$ and the biophysical properties can help determine the zero calibration of the measurement. This invention provides a method for calibrating the measurement of $\Delta\lambda$.

5. It provides a new, simpler apparatus for measuring optical properties of bioparticles. The invention provides an advantage over prior art to extract both size and refractive index properties of the bioparticle using multiple measurements in a single apparatus.

6. It provides a new method of operation for very small bioparticles of size less than the wavelength of light. The invention provides a new means for measuring physical properties of very small particles using light fluctuations arising from the interaction of bioparticles with the resonant light waves within the cavity.

7. It provides a new method for detecting, manipulating and separating bioparticles.

The invention makes use of arrays of micro- or nanocavity resonators acting as lasers to probe living cells and bioparticles. The arrays can also act as optical traps to simultaneously trap and analyze bioparticles or separate them from other species.

SUMMARY OF THE INVENTION (WITH OBJECTS AND ADVANTAGES)

It is an object of this invention to provide an analysis method for resonant optical devices that relates the measured optical parameter to the biophysical properties of the bioparticles. These biophysical properties include the size, refractive index (or polarizability) and the biomolecular composition. It is surprising and advantageous that using this method to analyze a population distribution of a single optical property, such as the refractive index, can indicate the state of health or disease in cells and/or organelles.

It is also an object of this method to extract the refractive index distribution from the measured laser wavelength shift $\Delta\lambda$ distribution. It is also a surprising advantage that a bioparticle (as small as hundreds of nanometers in size) can be individually and rapidly (in microseconds) measured for its refractive index. It is also a surprising advantage that the optical properties can be directly related to the biomolecular composition of the particle, and that the distribution of the optical property among a population of like particles can be well-described by simple, analytic statistical functions. When the biomolecular composition is altered as in a stressed or diseased cell, the optical properties and their distribution change in a manner that can be measured and analyzed with the statistical model.

It is also an object of this invention to make improvements to resonant cavity devices by incorporating methods for calibrating the measurements (providing a zero and scale factor) and for making corrections for any drift with time that may occur during the measurement procedure.

It is a further object of this invention to simplify the apparatus for measuring bioparticles by using a resonant optical cavity without a gain medium. This has the advantage of making the apparatus less costly to fabricate and facilitates both size and optical density measurement.

It is an object of this invention to provide the said analysis method to the improved apparatus and resonant optical device for the purpose of analyzing bioparticles.

It is also an object of this invention to provide a new method of operation of a micro/nano-cavity laser to analyze physical properties of very small bioparticles with size much less than the wavelength of light. The bioparticles can be in an external solution or inside living cells.

Finally, it is an object of this invention to provide a new method for simultaneous detection, analysis, and manipulation of the bioparticles in a micro/nanocavity optical resonator.

The present methods represent advantageous new ways to perform analyses of bioparticles and have wide ranging application for basic cell biology, cell culture, detection of disease, pathology, genetic engineering, environmental screening of toxins, pharmaceuticals, agricultural, and fermentation processes, biofuel production, and the like.

BRIEF DESCRIPTION OF THE DRAWINGS

The accompanying drawings and figures, which are incorporated in and form part of the specification, illustrate an embodiment of the present invention and together with the description, serve to explain the principles of the invention.

FIG. 1. Shows the estimated contribution to the refractive index of representative biomolecules in a cell or organelle.

FIGS. 11a, 11b, and 11c. Method for measuring properties of very small bioparticles.

FIG. 13. Method for measuring properties of living cells.

DETAILED DESCRIPTION OF THE INVENTION

Figure 2A:
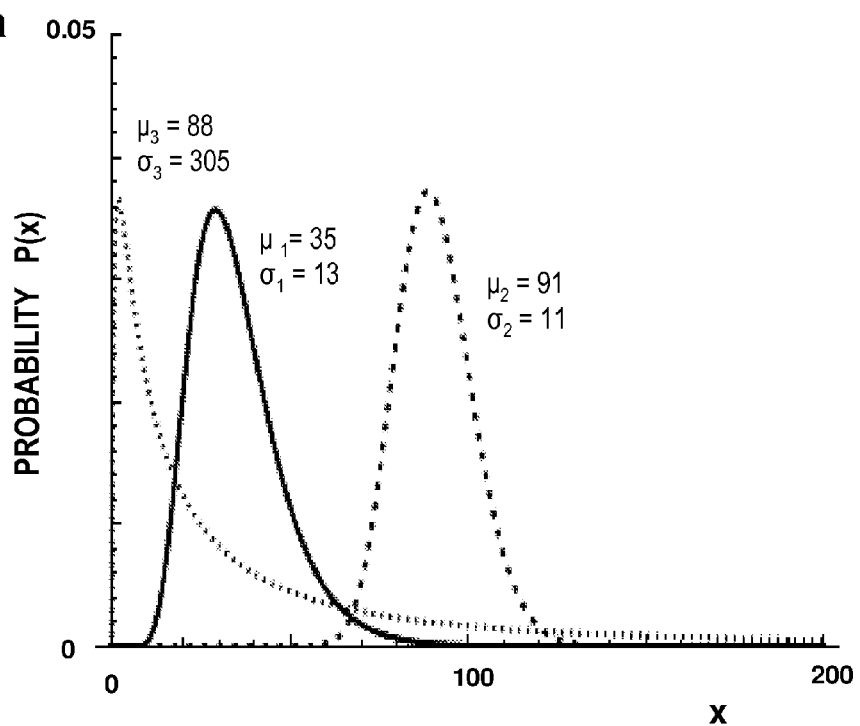
FIG. 2a Shows the probability distribution functions for normal peaks and a highly divergent distribution.

The optical properties of bioparticles depend upon their geometry and composition. Such bioparticles generally exhibit a variety of shapes and comprise a complex of biomolecules. Prior art describes how the morphology (spheres, rods, disks, or more complicated shapes) can be determined by imaging microscopy and/or spectroscopic methods. The detailed internal distribution of molecules, like proteins, can be determined by separate, more costly, measurements such as 2-dimensional gel electrophoresis. However, these measurements provide only the distribution averaged over a very large number of bioparticles (~$10^9$) and cannot provide information about the variance from particle to particle in a population. This variance is critical for assessing the degree of normality or abnormality of the bioparticle. The invention described here shows how to determine the variance of biophysical properties in a population of bioparticles. It shows how to separate size and index contributions to an optical measurement. It also shows how the refractive index is related to the overall biomolecular composition. And, it shows how to quantify the way in which dominant and other molecules contribute to the refractive index. And, it shows how changes in the biomolecular composition will change the refractive index. The invention also allows means for calibrating and maintaining the fidelity of measurements during operation of devices.

Refractive Index of Biomolecular Solutions

In the present method the optical refractive index of a bioparticle is examined. The refractive index is directly related to other optical properties (dielectric constant, polarizability, susceptibility, birefringence, nonlinear optical parameters and the like) of the particle, and this discussion can also apply to these properties. The speed of light through a biofluid or biological cell is inversely related to its biomolecular concentration. In general, the refractive index n is related to the molecular absorption coefficient $\beta = \epsilon M$, where $\epsilon$ is the molecular extinction coefficient and M the molecular concentration, by the Kramers-Kronig relationship $$n(\varepsilon) - 1 = \frac{hc}{2\pi^2} P \int_0^\infty \frac{\beta(\varepsilon')d\varepsilon'}{\varepsilon'^2 - \varepsilon^2} \tag{2}$$

where P is the principle value of the complex integral over photon energy $\epsilon'$, h is Planck's constant and c is the speed of light.

The refractive properties of biomolecules originate in the electronic structure of their internal chemical bonds. Estimates of the refractive index contribution of biomolecules to the total refractive index of a bioparticle are shown in FIG. 1. The vertical axis (from bottom to top) shows decreasing prevalency of the molecule (water, protein, lipid, etc). Most of the dry weight of a bioparticle is due to protein. Protein molecules possess covalent bonds that absorb strongly in the ultraviolet, but are mostly transparent in the visible and near infrared region where most semiconductors and solid state lasers emit. In general, the π-electron systems or proteins are the main origin of absorption in the 190-800 nm region. In small π-electron systems of proteins the absorption maximum occurs in the range 190-280 nm. The larger π-electron systems of the nucleic acid base units absorb near 260 nm and longer. Absorption beyond 400 nm occurs in the very large π-electron system of classes of chromophores and cytochromes that provide pigment to biomaterials. For example, many natural pigments arise from porphyrin and heterocyclic rings in chlorophyll, heme, and cytochrome oxidase found in mitochondria. The more extended larger π-electron systems of β-carotene absorbs between 400 and 500 nm. Previous experiments have shown that cytochrome complexes play an important role in the absorption spectra of cells and solubilized mitochondria in the visible and near infrared. These complexes comprise metal ions and large π bonds that delocalize electrons, lowering optical transition energies into the visible range, between 500 to 700 nanometers.

Refractive Index of Bioparticles with Complex Composition

Whole cells or organelles comprise a complex milieu of thousands of molecule types, including the heterocyclical molecular complexes and metal-containing porphyrin rings. The metal content of cells and mitochondria is found principally in the cytochrome proteins that are building blocks of complexes in the respiratory chain. These proteins play vital roles as reducing agents for normal metabolism for maintaining overall health of a cell. The large π systems of cytochromes play an important role in determining the refractive index in the visible and near infrared region of the spectrum where the particles are more transparent. And, each of the cytochrome molecules contributes to the refractive index at these wavelengths making it a sensitive measure of total cytochrome content. When certain genes are deleted or altered in cells or mitochondria, fundamental changes occur in cytochrome content and other pigmented molecules leading to changes in the refractive index that can be quantified by the optical properties.

Barer has shown a linear relationship between the refractive index and the biomolecular concentration as $n = n_0 + \alpha C$ where $n_0$ is the index of the solvent, $\alpha$ the specific refractive increment of the molecule (specified by Eq. 2 or determined empirically), and C the concentration in grams per 100 ml. A change occurs in index $\Delta n = \alpha \Delta C$ arising from a change in concentration in a particular molecular species. More generally, the refractive index of a bioparticle is given by the following equation, $$\Delta n_i = \sum_i \alpha_i C_i = \sum_{pigments} \alpha_{ci} C_{ci} + \sum_{proteins} \alpha_{pi} C_{pi} + \sum_{lipids} \alpha_{li} C_{li} + \ldots \quad (3)$$

where $\alpha_i$ is the specific refractive increment for biomolecule i (relative contributions vary as estimated in FIG. 1) and $C_i$ its concentration and the sum is over all biomolecules.

The refractive index contribution from a biomolecule increases as the product of the spectral weighting due to absorption in Eq. 1 and its concentration or biomolecular abundance in the bioparticle. Some structural biomolecules and osmolytes are tightly regulated by homeostasis, i.e. total water, protein, lipids, salt concentration and exhibit small uncertainty in abundance. These biomolecules form the basic cell structure and chemistry and require tight regulation to maintain cell viability. On the other hand, metabolic enzymes and metabolites exhibit a larger variation in abundance due to the existence of a wide dynamic range in respiratory states of cells or organelles like the mitochondrion. Some of these biomolecules vary several orders of magnitude in concentration without changing the basic structure or viability of the cell. These molecules typically occur in much lower abundance than the structural biomolecules.

Molecules with high spectral weight and abundance yield the highest optical density. Most of the functional structural molecules have high concentration but low spectral weight. On the other hand, respiratory enzymes containing pigmented biomolecules like cytochromes have high spectral weight but low abundance. Water is the primary contributor to the refractive index (accounting for 0.333), followed by structural proteins (about 0.06 to 0.08), cytochromes (about 0.007), and lipids (<0.005) and carbohydrates (<0.0002). These contributions are summarized in FIG. 1. Chromophores and cytochromes stand out as unusual biomolecules because they are present in lower abundance but have the highest spectral weight for the refractive index in the visible and near infrared region of the spectrum where optical resonators operate.

Thermodynamics and Statistical Distributions of Molecules in Cells, Organelles, and Bioparticles A cell, organelle or bioparticle comprising a membrane bound solution of biomolecules has a refractive index that is higher than its surrounding fluid. This arises from a basic biological function of the cell membrane to selectively uptake of ions or molecules from the environment to concentrate them in the interior and assemble them into new biomolecules for increasing the cell functionality. A variety of passive and active mechanisms are used to establish these concentration differences, which in turn produce a differential pressure across the membrane. In thermodynamic terms, a function W can be defined that is the probability of finding a cell with a given biomolecular concentration C at a temperature T surrounded by a solution of concentration $C_0$. The theory of dilute solutions is used to illustrate this model. The osmotic pressure, here used loosely for any molecule enclosed by a semi-permeable boundary, is $P = (C - C_0)kT$ which is the well known van't Hoff relation. The net energy to raise the concentration from $C_0$ to C against the diffusive force is PV where V is the cell volume. If an ensemble of cells was treated in analogy to a population of particles in thermal equilibrium, the chemical potentials of the cytosols of each cell would be equal to the chemical potential of the exterior solution. In this case the differential probability of finding a cell with energy E is proportional to $\exp(-E/kT)$. The probability distribution would take the form $\Omega(\Delta C)\exp(-\Delta CV) \approx Q(N)\exp(-N)$ where N is the number of molecules. $\Omega$ is the number of accessible states, a rapidly increasing function of N conspiring with the exponential to produce a sharply peaked function in N. These arguments apply to precursor molecules and to biomolecules assembled from them.

Statistical physics can be used to describe this peaked function as the fluctuations in N, similar to fluctuations of particles in a gas or solutes in a dilute solution. The distribution in a fixed volume is $$W(N) = (1/\sqrt{2\pi})\exp(-(N-\overline{N})^2/2N) \quad (4)$$

where N is the total number of solute particles and $\overline{N}$ is the mean value of N. This distribution assumes that the volume of the cell is sufficiently large so that the deviation $N - \overline{N}$ is small compared with N. This is the case for large cells that contain the order of $\sim 10^{10}$ molecules like hemoglobin proteins in a red blood cell. There may be additional homeostatic regulatory mechanisms that place other restrictions on the deviations. On the other hand, there may be cells or organelles of much smaller volume such that the deviation is large compared to the mean. In this case, the distribution is given by Poisson's formula, $$W(N) = \overline{N}^N \exp(-N)/N! \quad (5)$$

In this case, the distribution exhibits an asymmetric shape with a cutoff near low N and a long tail for high values of N. For example, mitochondria have volume ~$10^{-13}$ cm$^3$ with the number of biomolecules of a given prevalent type ranging from $10^2$ to $10^5$. Yeast cells have volume ~$10^{-10}$ cm$^3$ and biomolecules numbers some 3 orders of magnitude higher.

Statistical Distributions of Optical Properties of Bioparticles

The preceding discussion explains ideal distribution probabilities of molecules within cells. In biophysical experiments, the number of molecules may not be directly measured. Instead, an optical property (fluorescent intensity, optical density, phase contrast, spectral property or the like) may be more accessible. In this case, the probability distribution of the measured property has a more complicated dependence on geometry as well as biomolecular composition. A typical measured optical variable like a wavelength displacement or fringe shift or phase change or the like (collectively represented here by the variable $\Delta\lambda$) depends on the product of the particle diameter d and index difference $\Delta n$ as $\Delta\lambda = kd\Delta n$ where k is some factor specific to the particular optical variable being measured. Thus, $\Delta\lambda$ is expected to be the product of 2 or more independent and randomly distributed variables. In many cases d is a normally distributed variable.

If the $C_i$ are normally distributed variables (since V, and N from Eq 2 are), then so is $\Delta n$, with $\mu = \Sigma\mu_i$ and $\sigma^2 = \Sigma\sigma_i^2$. The distribution then takes the form of a convolution integral of variables d (distributed with mean $\Xi_d$ and deviation $\sigma_d$) and $\Delta n = \Delta\lambda/kd$ (distributed with mean $\mu_{\Delta n}$ and deviation $\sigma_{\Delta n}$), $$P_1(D) = Ae^{-(D-\mu_D)^2/2\sigma_D^2} \qquad (6)$$

$$P_2(\Delta n) = Be^{-(\Delta n - \mu_{\Delta n})^2/2\sigma_{\Delta n}^2} \qquad (7)$$

$$P_{12}(\Delta\lambda) = AB\int_{-\infty}^{\infty} P_1(D)P_2(\Delta\lambda/kD)dD \qquad (8)$$

This distribution function can be approximated through a transformation of $\Delta\lambda \to x = \exp(\Delta\lambda)$ that results in a log-normal distribution of the form $$P(x) = \frac{1}{x\sigma'\sqrt{2\pi}} e^{-(\ln x - \mu')^2/2\sigma'^2} \qquad (9)$$

where x is the fitting variable, and $\mu'$ and $\sigma'$ are the log-normal fitting parameters. The Log-normal transformations $\mu = \exp(\mu' + \sigma'^2/2)$ and $\sigma^2 = (\exp\sigma'^2 - 1)\exp(2\mu' + \sigma'^2)$ are used to find the physical mean, standard deviation and variance of $\Delta\lambda$ of the distribution.

The log-normal probability function P(x) is illustrated in FIG. 2a for three cases where the ratio $\mu/\sigma$ of the mean $\mu$ to the standard deviation $\sigma$ varies from a small to large value. For an intermediate value (solid curve with $\mu/\sigma=2.7$) the distribution reveals a peak with long tail for large x. For larger ratios (large dashed curve with $\mu/\sigma=8.3$) the distribution reveals a more symmetrical peak. Both of these distributions represent a normal or regulated distribution where the mean is larger than the standard deviation. For small ratios (small dashed curve $\mu/\sigma=0.29$) the distribution exhibits a peak near the origin that is highly skewed to large x. This distribution applied to bioparticles is called a biomolecular divergence, for reasons explained later.

Figure 2B:
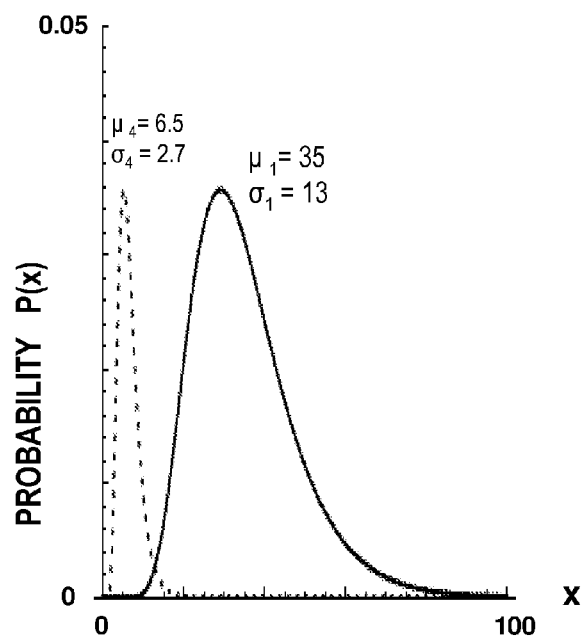
FIG. 2b Shows the probability distribution function representing for a normal peak and highly collapsed distribution.

FIG. 2b Shows the probability distribution function representing changes from normal, well-regulated biomolecular distribution among bioparticles (solid curve) to a highly collapsed distribution (dashed curve) characteristic of a second type of abnormal state (biomolecular collapse). These log-normal distributions show mean p and standard deviation $\sigma$ parameters:

(1) Solid curve $\mu/\sigma=35/13=2.7$ showing a peak with long tail for large x. (2) Dashed curve $\mu/\sigma=6.5/2.7=2.41$ showing a peak collapsed to near the origin.

FIGS. 2a and 2b illustrate two types of changes, divergence and collapse, that may occur as a result of biomolecular changes from a normal or regulated distribution. Other types of distributions are possible and might be described by other statistical functions beyond the log-normal distribution. The invention is not limited to log-normal distributions in the analysis.

Examples of Distributions Found in Practice

Figure 3:
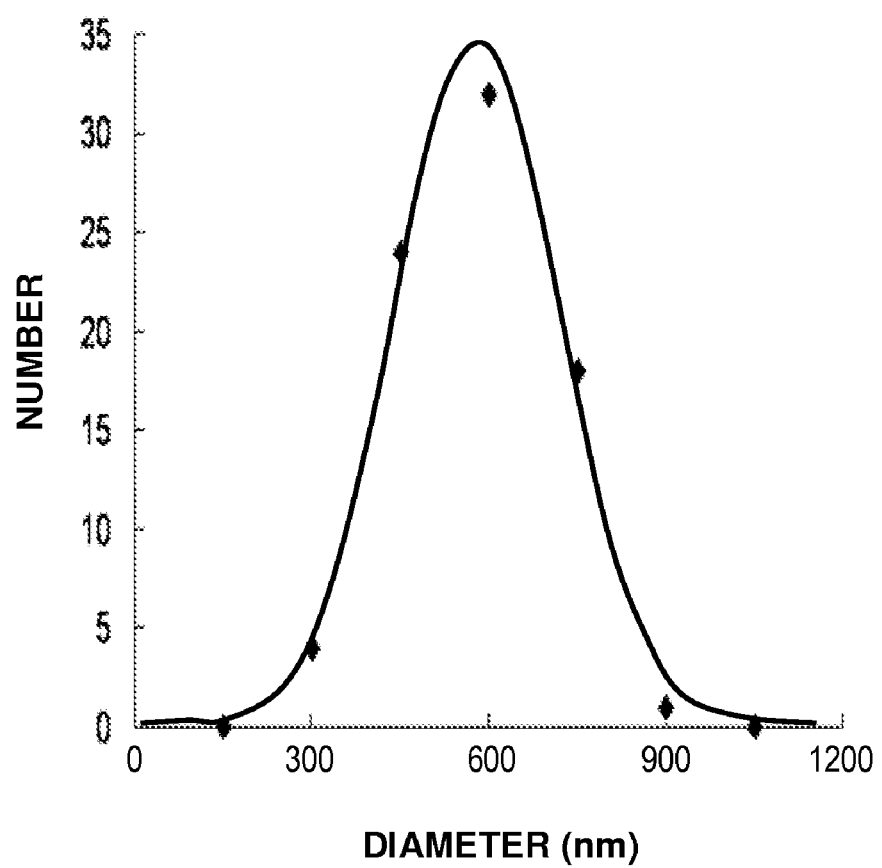
FIG. 3. Shows a histogram of measured mitochondrial diameters.

Several classes of distributions for refractive bioparticles can be indentified. A first class is a homogeneous (or intrinsic) distribution of bioparticles of similar type. These may be uniform in size (narrow size distribution) but less uniform in optical properties. This is a common case observed in experiments. For example, mitochondria fragment into nearly uniform-sized particles when the cells are stressed or when the mitochondria are extracted from the cells. Such a particle distribution is shown in FIG. 3.

Another example is the distribution of red blood cells that commonly occur with uniform biconcave geometries. Here the physical size is more tightly regulated than the biomolecular composition. The joint distribution (size and index) is reflective of the optical properties. On the other hand, the distribution may be uniform in optics (biomolecular composition) but comprise a broad distribution of sizes. In this case the joint distribution is more reflective of the size. This second case is less common. It is also possible to have both distributions exhibit a broad range. A second class of inhomogeneous (or extrinsic) distributions includes two or more dissimilar bioparticle types. In this case the distribution would be an additive superposition of multiple peaks representing each type. It would be possible to extract each component distribution by fitting the inhomogeneous distribution with a superposition of homogeneous distributions.

Another type of inhomogeneous distribution can occur within a homogeneous population when the individual bioparticles tend to aggregate or form clusters with two or more bioparticles. In this case the measured distribution is sensitive to the measurement technique. For example, high resolution imaging or nonlinear optical methods are still able to resolve individual bioparticles as they are sensitive to the bioparticle boundaries. Also the technique may sensitive to 2-dimensional or 3-dimensional effects and able to resolve the geometry of the cluster. On the other hand, some techniques (like total fluorescence intensity measurements) would only measure the total cluster volume and not measure individual bioparticle properties. However, it might still be possible to resolve discrete multiples of particles in the distribution of clusters.

The probability distribution for the particle size and/or the index difference may not be a normal distribution. In this case the analysis is more complicated, but the two distributions can still be approximately determined. The particle size distribution can be measured by some other technique like imaging microscopy (optical, confocal, near field optical, electron, atomic tunneling or force, or the like) or by flow cytometer or sizing methods or the like. Then, the measured distribution for the optical variable (fringe shift, wavelength shift, phase or contrast change, etc) can be deconvolved using the measured particle size distribution to render a probability distribution for the refractive index difference.

Spectroscopy Embodiment to Measure Optical Properties

Figure 4:
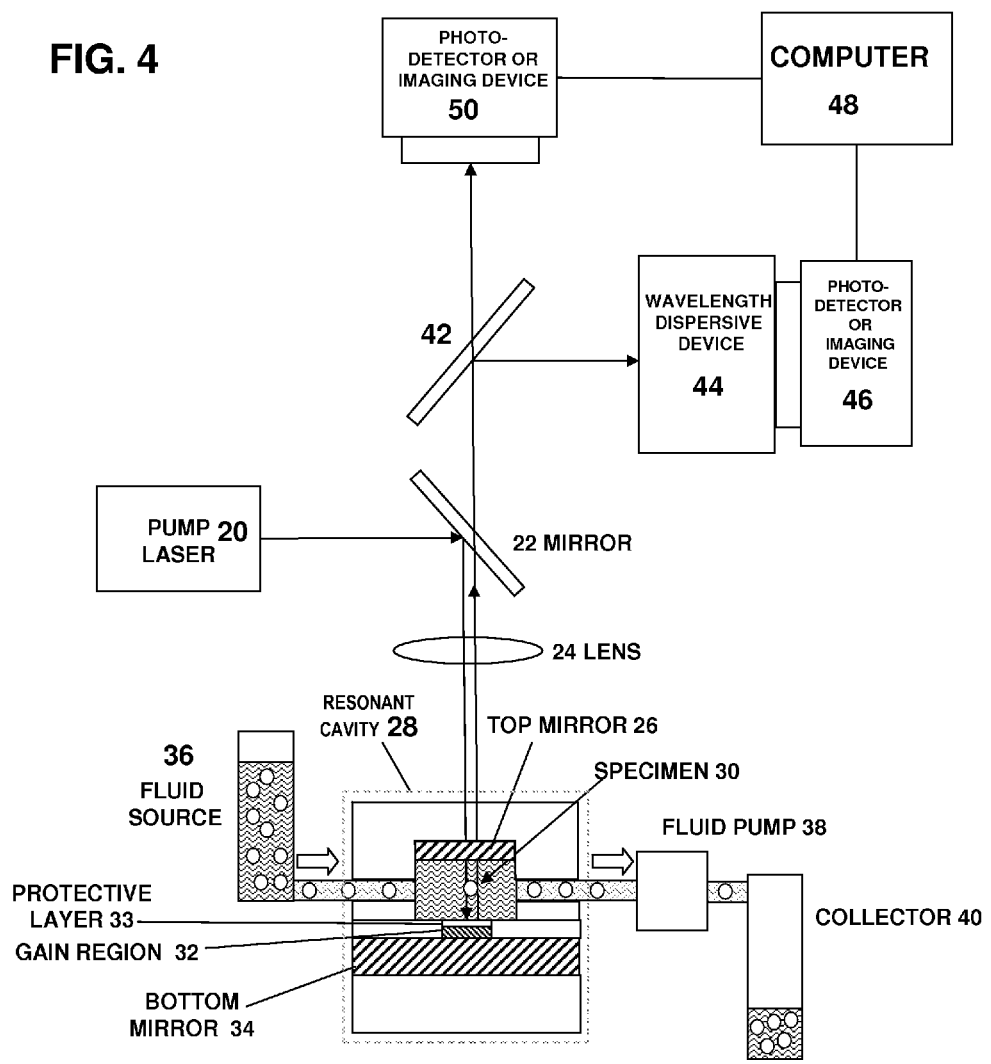
FIG. 4. Schematic of a biocavity laser apparatus.

An apparatus to measure optical properties of particles is shown in FIG. 4. It comprises a pump laser 20 emitting a beam that is directed by a beam splitter 22 through a lens 24 to a biocavity laser (resonant cavity 28) comprising a top mirror 26, a specimen in an specimen analysis region 30, a gain region 32 comprising a semiconductor and waterproof protective overlayer 33 (oxide, nitride, polymer, polyethylene glycol or polydimethylsilane, or organic compound), and a bottom mirror 34. Particles from a fluidic source container 36 flow through the analysis region with the help of a pump 38 to a collector 40. During transit, the particle passes through a gain region and triggers the biocavity laser to emit an intense beam that passes out of the cavity to a beamsplitter 42 where it is directed to an imaging device 50 and/or a wavelength dispersive photodetective device 44/46. Data from these devices are fed to a computer 48 for subsequent analysis. In the operation of the biocavity laser, the higher refractive index of a bioparticle (relative to the cavity with fluid only) triggers a lasing spectrum, and the spectrum is red-shifted relative to the cavity resonance without the bioparticle.

The laser technique has two critically important features. First, it is sensitive to small changes in biomecular composition of cells. Tiny changes in laser wavelength can be detected since the laser linewidth is very narrow. So, the method is able to detect small biomolecular changes that occur with, stress, disease, or genetic manipulation. Second, the laser is sensitive to very small objects such as organelles like mitochondria and exploits a newly discovered nano-optical transduction method. Basically, this ultrasensitive detection of submicron particles uses "nano-squeezing" of light into photon modes imposed by ultrasmall dimensions in a submicron laser cavity. The condition for nano-squeezing is that the organelle must be approximately smaller than the wavelength of light. This is a critical advantage of the biocavity laser. Because bioparticles like the mitochondria are so tiny (about 500 nm in diameter), it has been difficult to study them using standard light microscope or flow cytometry techniques. And, electron or atomic force microscopies may be limited to nonviable, fixed organelles so they cannot reproduce physiologic measurements. Thus the biocavity laser is an ideal tool for studying biomolecular changes in viable bioparticles.

The laser technique has a number of surprising features. The measurements can be self-triggering and self-calibrating and can be made in real time as particles flow in a microcavity. This is enabled by machine vision techniques whereby an algorithm can use binary image maps to located spectral position, peak width, and intensity and can be performed quickly. Further, the method is resistant to clustering of particles because of the nonlinear nature of the lasing process that requires a membrane-bounded bioparticle to operate.

Practical Results Obtained with Spectroscopic Embodiment

Experiments were performed to demonstrate the utility of biocavity laser spectroscopy to rapidly measure the effect of genetic disturbances in mitochondrial function. In one experiment a pair of mouse liver cell lines was used. One line was normal and the other line was transformed to cancer cells by carcinogens. The two cell lines were grown in separate, adherent tissue cultures. After growth to a large number of cells, the cells were removed from the tissue culture and suspended in solution. This removal has the effect of stressing the mitochondria which fragment into small particles of nearly the same size. That mitochondria fragment into nearly uniform-sized particles when cells are stressed is a surprising advantage that simplifies measure of optical properties. The mitochondria were removed from the cells for subsequent analysis by biocavity laser spectroscopy.

Micrographs of the isolated mitochondria were obtained by fluorescently labeling the mitochondria. FIG. 3 shows a histogram of the measured distribution of particle sizes, showing a mean diameter near 600 nm and a standard deviation of about 100 nm. The histograms is well-described by a normal Gaussian distribution (solid line). The mitochondria were suspended in phosphate buffered saline (PBS) without calcium or magnesium and flowed through the biocavity laser. Spectra were collected and the resulting laser peak shifts $\Delta\lambda$ (relative to fluid-only) were analyzed. Delta $\lambda$ is measured in nanometers as the difference between the reference wavelength of the biocavity laser, and the wavelength of red-shifted laser light that cells or mitochondria emit as they flow through the biocavity laser. It is a function of the refractive index difference between the cells or mitochondria, and the surrounding aqueous medium (PBS) and particle size. Since refractive index is a function of biomolecular composition and concentration, mitochondria that contain more chromophores and cytochromes will show greater peak shifts.

Figure 5A:
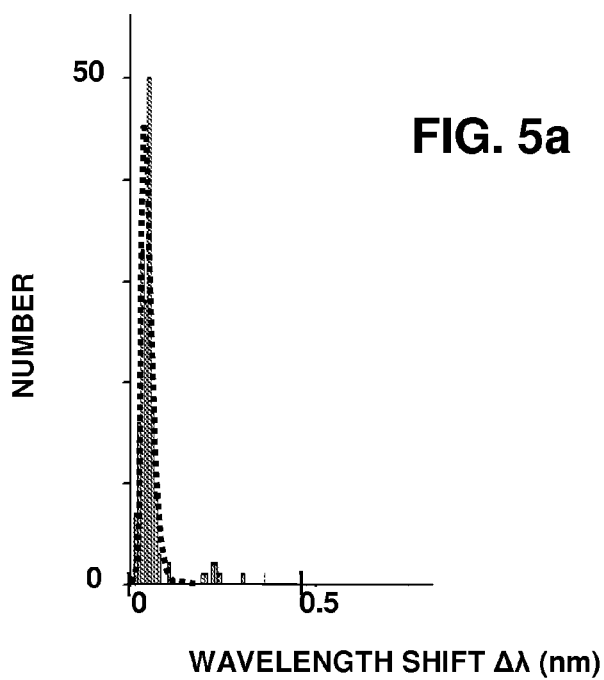
FIG. 5. Histograms of laser wavelength shifts for isolated mitochondria from cancer (FIG. 5a) and normal (FIG. 5b) mouse liver cells.
Figure 5B:
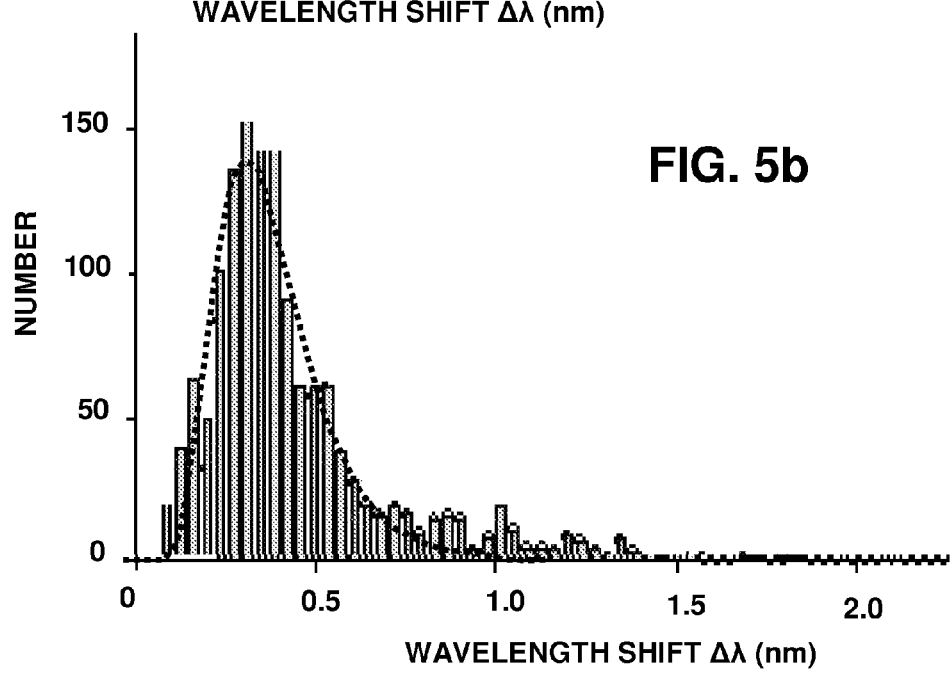

The statistical variation of $\Delta\lambda$ within each population was studied and modeled. The population distributions of $\Delta\lambda$ obtained with mitochondria from normal cells (FIG. 5a) and cancer cells (FIG. 5b) reveal striking differences in mean and standard deviation. Normal mitochondria produced a distribution with a single peak with mean near 0.4 nm and tail to longer wavelength. The shape of this distribution can be fit with a log-normal distribution. In contrast, abnormal mitochondria produce a peaked distribution with a drastically 10 times lower mean value and standard deviation. These features reflect a collapsed state of stressed or diseased cells that have a greatly changed composition of biomolecules in the mitochondria. This altered composition reflects a large decrease in biomolecules like chromophores and cytochromes that contribute to the refractive index. The loss of these molecules in the mitochondria represents a greatly lowered biochemical reducing ability of the electron transport chain. This represents an altered metabolic state of the diseased cell. These observed changes observed in the spectra of normal healthy mitochondria to those of mitochondria in the cancer state indicate that the technique has the ability to rapidly diagnosis healthy and disease states.

The log-normal distribution provides the best, self-consistent fitting function to these data. The fitting function (dotted lines) shown in FIG. 5 accurately describe the shapes of the measured distribution functions. The single fitting function Eq. 9 with only 2 adjustable shape parameters describe the date much better than Gaussian or Poisson functions discussed earlier.

Another experiment was carried out to simulate the effect of neurological diseases effects like Alzheimer's disease on mitochondria. In the electron transport chain of the mitochondria, a potential is established by internal membrane pumps that transport protons across the inner membrane. Exposing mitochondria to high $Ca^{++}$ gradients causes breakdown of an inner mitochondrial membrane potential, with attendant creation of megapores, organelle swelling, and release of toxic cytochrome c into the cytoplasm. In an experiment, mitochondrial isolated from a separate line of mouse liver cells were suspended in a buffer solution for flow experiments. One suspension was used as the control. And a separate solution of CaCl ranging from 10 to 1000 µM was added to produce an insult to the organelle and induce formation of a megapore and swelling. The organelles were flowed for a few minutes and the emitted spectra were recorded and analyzed to extract spectral parameters such as spectral wavelength, linewidth, intensity and others. These parameters were summarized in histograms shown in FIG. 6b (normal) and 6a ($Ca^{++}$ insulted) to show the parameter mean values and their statistical variation among the cell suspension.

Figure 6A:
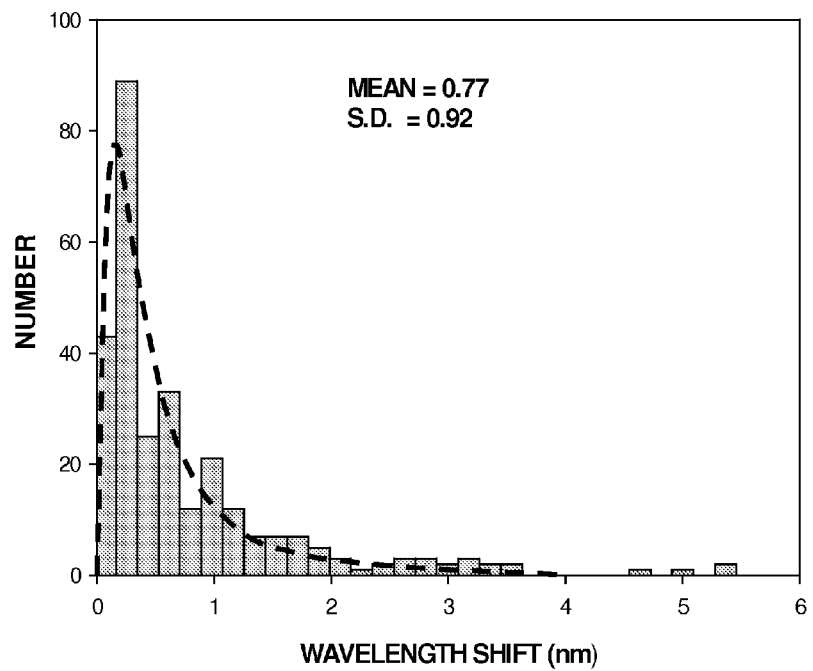
FIG. 6. Histograms of laser wavelength shifts for mitochondria isolated from normal mouse liver cells (FIG. 6b) and then subjected to Ca++ concentrations to simulate a disease state (FIG. 6a).
Figure 6B:
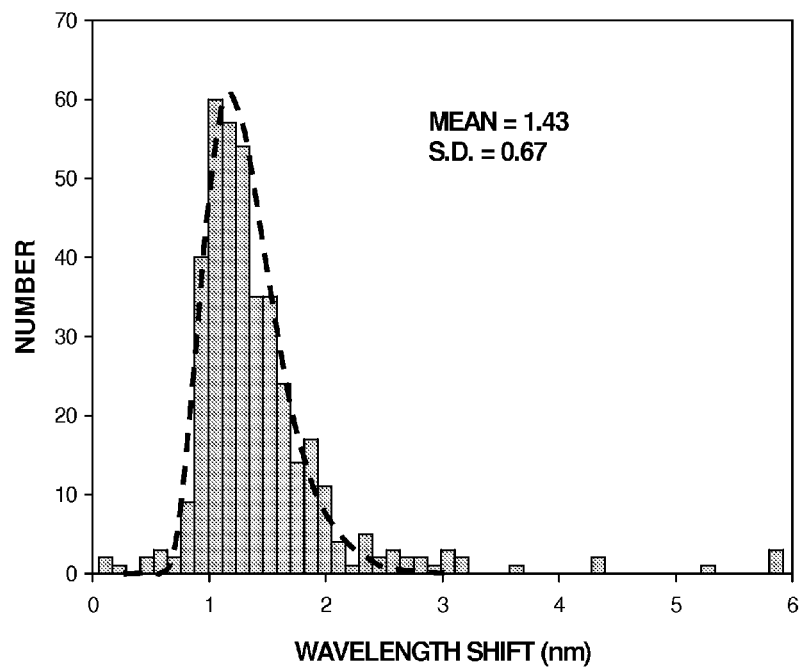

These data show that the control suspension without $Ca^{++}$ reveal a singe $\Delta\lambda$ peak near 1.4 nm wavelength shift with standard deviation of about 0.67 nm. The histogram is well described by a log-normal distribution (dashed line). The histogram for the control mitochondria suspension with the addition of a 1000 μM $Ca^{++}$ solution is shown in FIG. 6a. These data are significantly changed from the control sample and exhibit a lower mean and much larger variance. These insulted mitochondria exhibit a biomolecular divergence whereby $\Delta\lambda$ is peaked near 0 but is spread to much larger values as well. This distribution is also well described by a log-normal distribution (dashed line) with lower mean and larger standard deviation. Using the log-normal analysis of these data clearly shows that the optical density in the mitochondria has changed due to decreases in their refractive index and biomolecular composition. The biomolecular composition changes because the organelles swell and lose cytochrome content. The statistical analysis provides guidance in calibrating the spectra as well as the determining the shape of the distribution.

Calibration of the Measurements

Once the distribution of $\Delta\lambda$ is measured, it is important to calibrate the spectral distribution. The calibration scale comprises a zero and a scale factor. The scale factor can be set by using a calibrated spectrometer or the like or measuring system response for two or more sources with known wavelengths. Determining the zero is more difficult. Prior art used a spontaneous emission wavelength set by a longitudinal mode of the resonant cavity without a bioparticle.

Alternately, prior art used stimulated emission near a longitudinal mode. These reference wavelengths are helpful, but do not necessarily determine the zero wavelength with high precision.

With regard to calibrating the zero position, it is important to measure and correct for any drift with time that may occur during the measurement. One method to determine the zero is to measure a pre-existing cavity mode that is independent of the bioparticle. By tracking such a mode as a function of time during the measurement, it is possible account for any drift or sudden perturbation of the cavity. In this case, either a spontaneous or stimulated emission wavelength established by the resonant cavity independent of the particle being measure is recorded as a function of time. This measurement can be recorded simultaneously or periodically with the measurement of $\Delta\lambda$ for the particle or measured periodically and then interpolated for an arbitrary time. Thus a reference wavelength is available for every measured shift arising from a bioparticle. This enables the system drift with time to be can be determined. Then, the measured spectra can be corrected for any effects of drift.

In the absence of a reference mode, a method for calibrating the zero is to use a homogenous fluidic specimen. In this case, each small volume of the fluid containing many bioparticles (the order of hundreds) is representative of the properties of the whole sample volume. Each small volume sample has the same average properties. The moving average of each small volume can then be used to correct for drift of the zero calibration. Another method of calibrating the zero is to fit the moving distribution of several volumes with the probability function using zero as an adjustable parameter. Knowing the form of the distribution function enables the zero to be determined with higher precision. Using this method, it is possible to accurately record the experimental distribution of measured values of wavelength shift without measuring any reference wavelength.

Microscopy Embodiment

Figure 7:
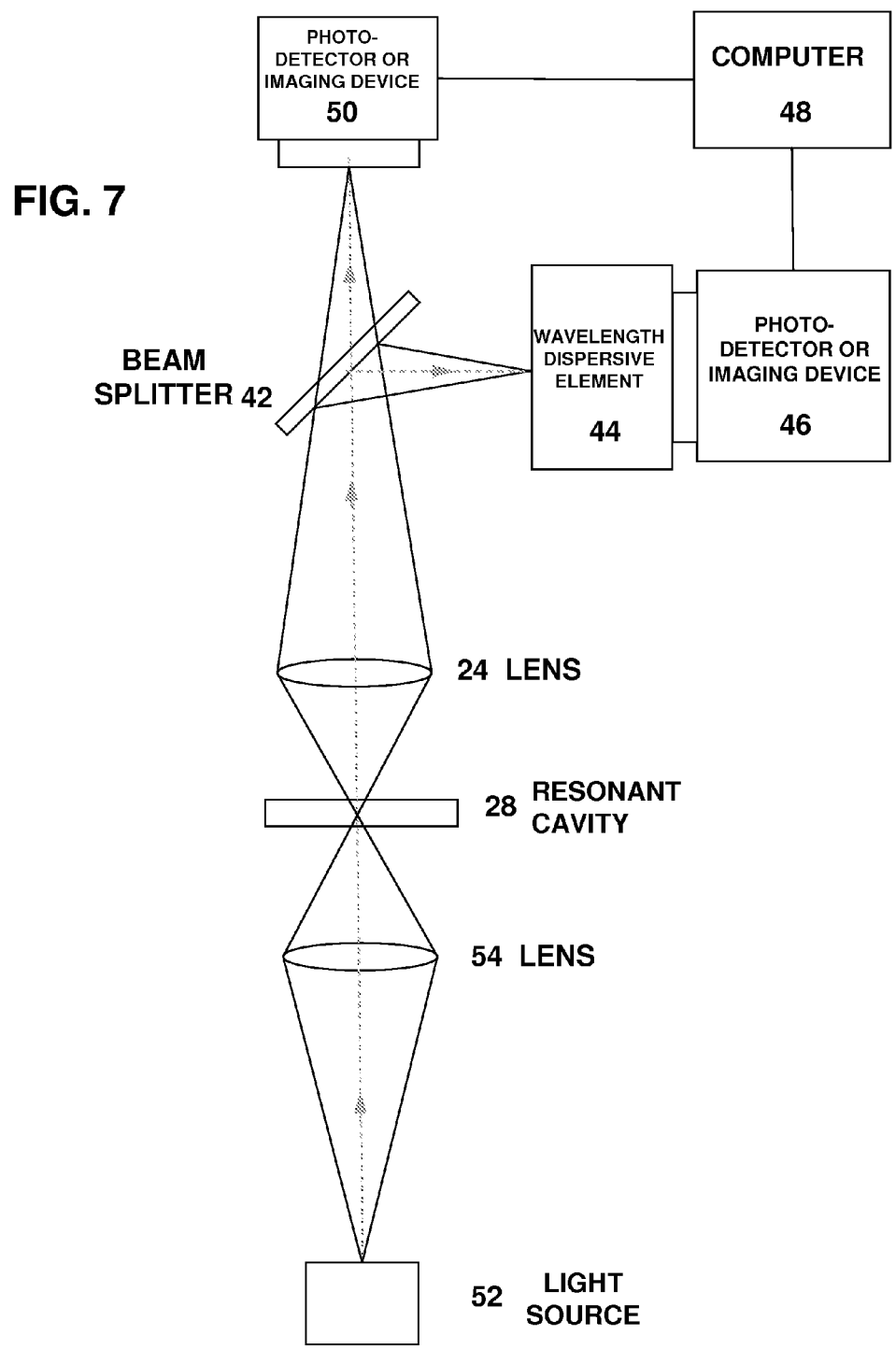
FIG. 7. Apparatus for measuring optical properties of bioparticles in a resonant optical cavity.
Figure 8A:
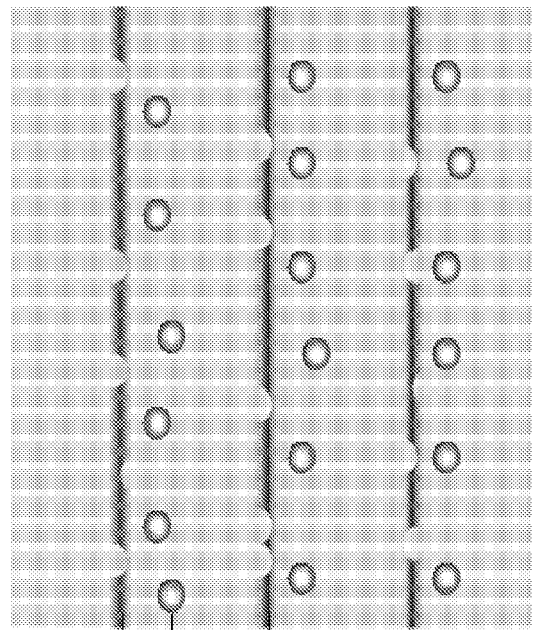
FIG. 8. Schematic of a graded, resonant optical cavity for measuring optical properties of bioparticles, (top view FIG. 8a and side view in FIG. 8b) and binary image from an experimental cavity (FIG. 8c).
Figure 8C:
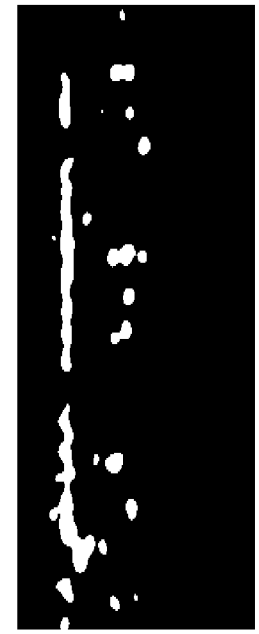
Figure 8B:
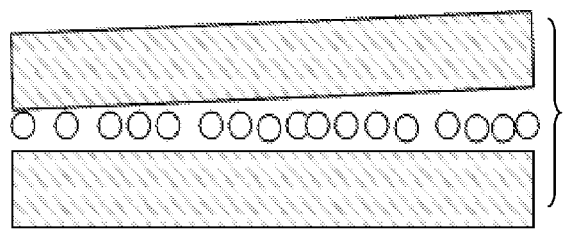
Figure 9:
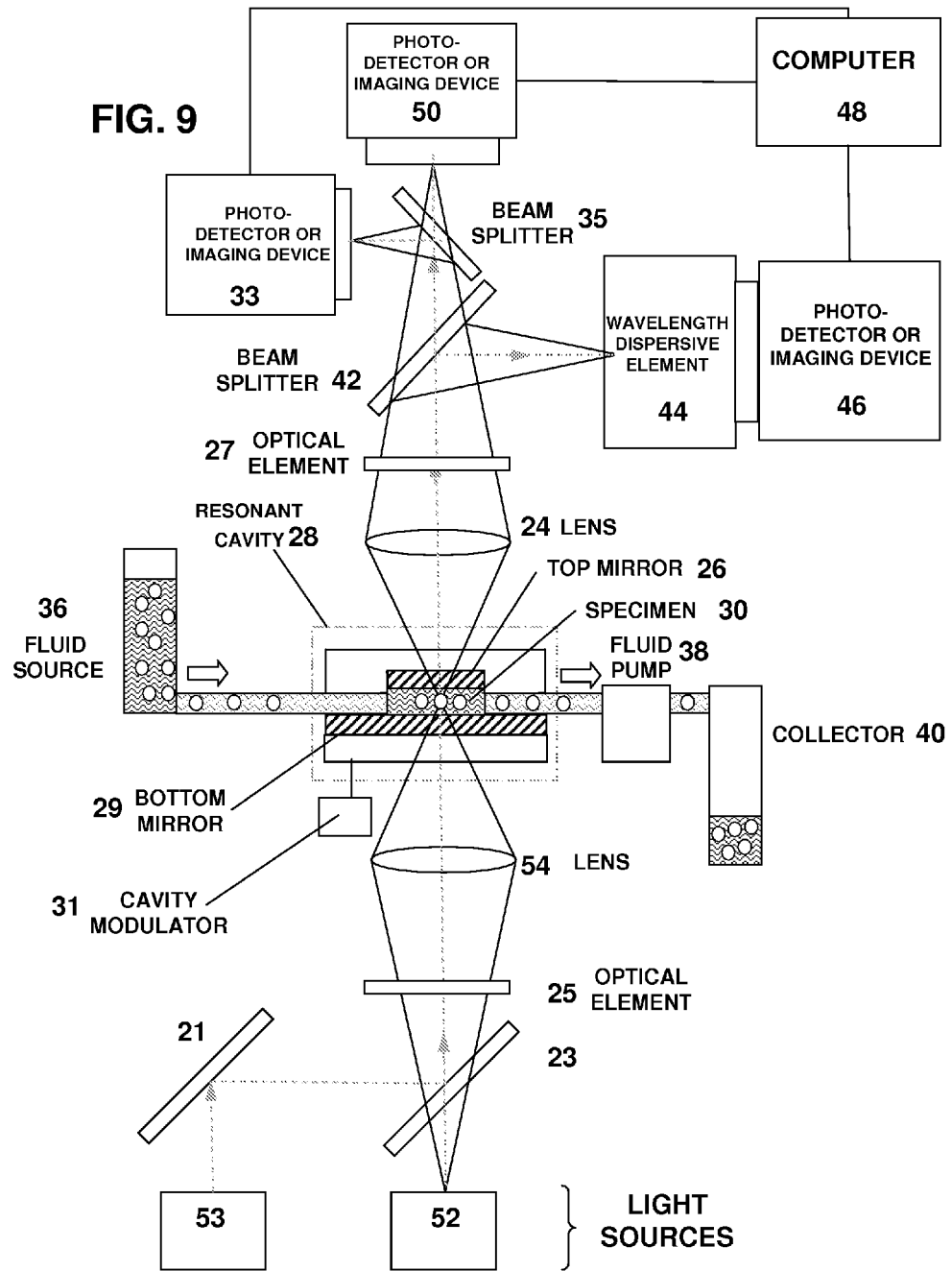
FIG. 9. Enhanced apparatus for measuring optical properties of bioparticles
Figure 10B:
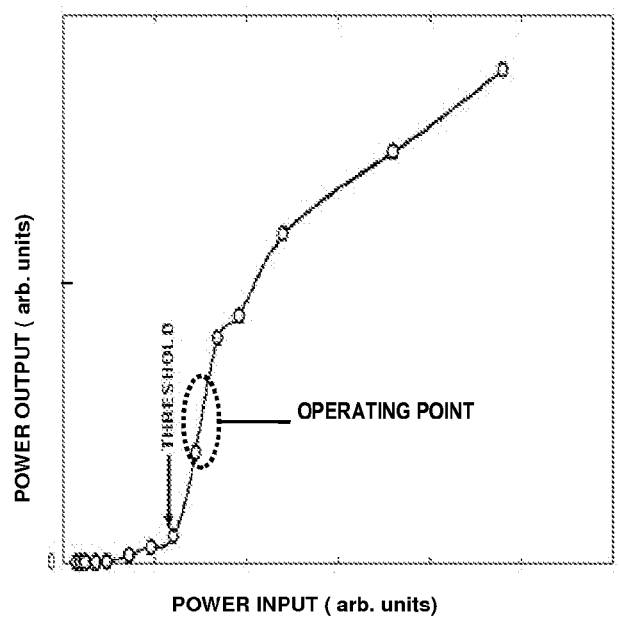
FIGS. 10a and 10b. Nanolaser for measuring properties of very small bioparticles.
Figure 10A:
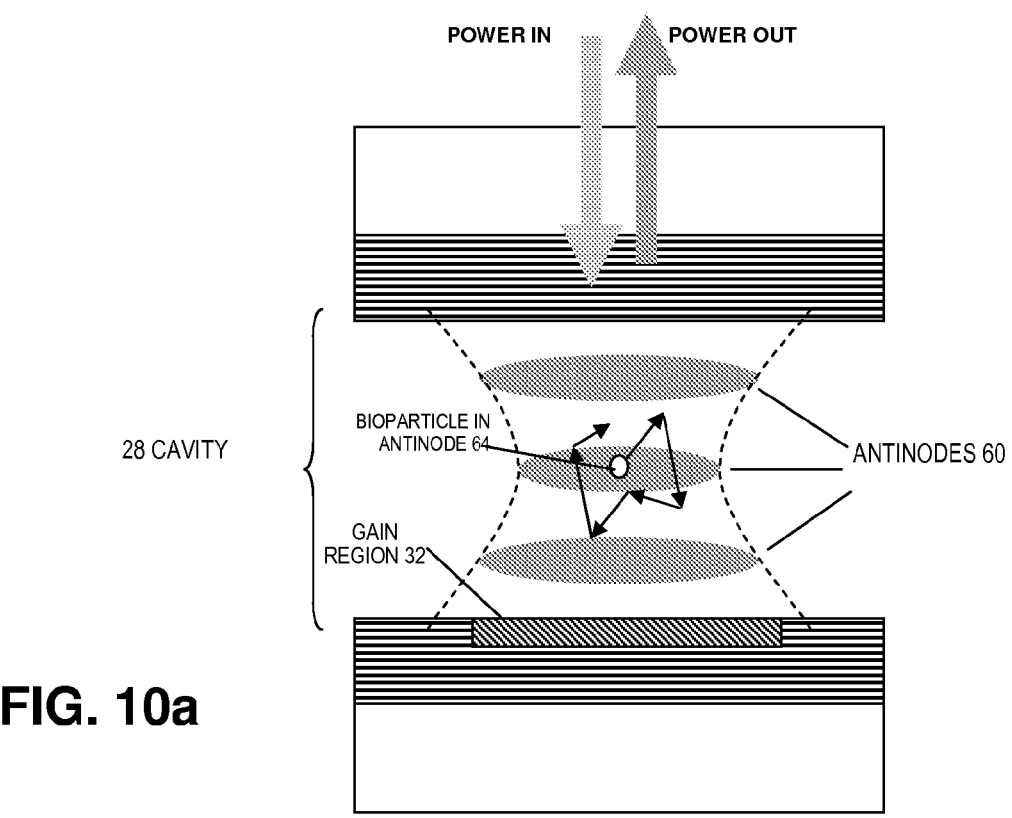
Figure 12:
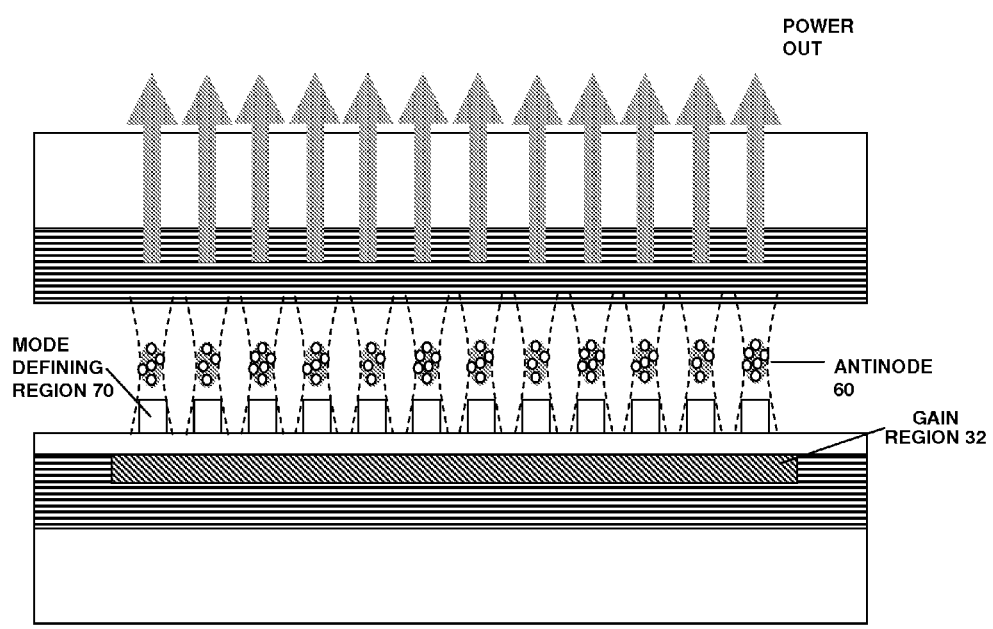
FIG. 12. Method for simultaneously detecting, analyzing, and manipulating bioparticles using intracavity resonant wave optical trapping.

Another embodiment of the measurement and analysis method is to use interference microscopy with an apparatus shown in FIGS. 7 through 9. In FIG. 7 light from source 52 is directed toward a resonant cavity (with or without gain) 28 with lens 54 and then the image of the cavity is relayed with lens 24 to an imaging device 50 and/or to a spectroscopy/detector device 44/46. The output of these devices is linked to a computer 48 for analysis. The light source could be a laser, LED, lamp, fiber optic source or the like. Alternately the light source could be contained in the cavity (semiconductor, fluorescent material, or the like). The light interacts with the cavity to establish optical resonances that can be observed by a detector. These conditions can be detected by the imaging device or spectral device. When bioparticles are inserted into the cavity, the light interacts with the particle/cavity and produces a light signal (transmitted, reflected, scattered, fluorescence or the like) that is modified by the bioparticle and can be analyzed by spectrometer or microscope equipped with a photosensitive detector (PMT, PD, video camera, CCD, or the like) to record images. FIG. 7 shows a transmittance apparatus but the invention is not limited to this arrangement and could also take the form of a reflectance, scattering, or fluorescence arrangement or combination thereof.

In one embodiment, the resonator is preassembled and the specimen is brought into and out of the resonator, usually in a fluid by force of injection, flow, pump, vacuum, gravity, electrokinetic, or the like. In another embodiment, the resonator is not preassembled but comprises components. The specimen is applied to the components, for example, by application of a fluid onto a surface using a drop, smear, brush appliqué, paint-on, spray, or the like. The specimen may remain wet or be allowed to dry, and the resonator is assembled to contain the specimen for further analysis.

If the cavity dimension is graded in space, the resonance conditions are mapped across a 2-dimensional space for a planar cavity. The resonance conditions render images with a variety of intensity variations. The locus of intensity maxima occur as contours where the cavity is in resonance. There is a dark background where the cavity is out of resonance. With bioparticles present, the contours are locally altered. Some particles shift the cavity out of resonance while others shift it into resonance. This is illustrated in FIG. 8 for a simple graded planar cavity where the resonance conditions are rendered as spaced interference fringe images. The resonance conditions in a medium of refractive index $n_1$ for neighboring fringes in the cavity with spacings $d_1$ and $d_2$, respectively are $$n_1 d_1 = m\lambda/2 \tag{10}$$

$$n_1 d_2 = (m+1)\lambda/2 \tag{11}$$

where m is the order of the fringe and $\lambda$ is the wavelength of light. The spacing L of the fringes is given by $$d_2 - d_1 = L \sin\theta \tag{12}$$

where $\theta$ is the wedge angle of the graded cavity shown in FIG. 8b. When an object of height h and index $n_2$ is placed into the cavity, the fringes will be locally displaced at the object as in FIG. 8a. If the optical thickness $h\Delta n$ where $\Delta n = n_2 - n_1$ is small compared to the optical thickness of the cavity $n_1 d$ then the observed fringe displacement $\Delta L$ will be less than L and determined by the relationship $$h\Delta n = \Delta L/L \lambda/2 \tag{13}$$

Thus, the optical thickness of the object is the relative fringe displacement $\Delta L/L$ times a half wavelength. If the particle height is known, the index can be determined from the fringe displacement. For a group of said objects (cells, organelles, bioparticle or the like) the statistical distribution of the refractive index can be determined from the distribution of bioparticle-induced fringe shifts (FIG. 8c) as described in a previous section of this application.

Another embodiment of the apparatus is shown in FIG. 9. FIG. 9 also includes multiple light sources 52 and 53 and multiple detectors 50, 33, 44/46 and multiple beamsplitters 21, 22, 42 and 35 for recording combinations of light wavelengths for imaging/spectral measurements of transmittance, reflectance, scatter, diffraction, phase, absorption, fluorescence or the like. When used in combination with the resonance measurements, these additional measurements provide advantages in identifying bioparticles and measuring additional optical properties FIG. 9 also includes means for flow of bioparticles using elements 36, 38, and 40 to allow bioparticles to be injected or flowed through the cavity. FIG. 9 includes imaging (elements 33 and 50) and spectral means (elements 44 and 46) for detecting resonance conditions. It also includes a computer 48 for analysis including machine vision methods.

FIG. 9 also includes a means (element 31) to modulate the cavity spacing, geometry, phase, reflectivity, Q or the like to enhance measurements of large numbers of particles. For example, the resonance conditions can be modulated across the field of view by scanning the cavity spacing d by mechanical, acoustic, electrical, magnetic, piezoelectric, optical, or other means. This has the effect of moving the fringes across the field of view such that more particles can be analyzed. In this case the local fringe displacement by a particle is recorded in successive images of moving fringes. It is also possible to scan the cavity in space, scan the light source in space or in wavelength to expedite the analysis.

FIG. 9 also includes means (element 25) for modulating, steering, scanning, pulsing or holographic control of the input light. It also includes a means (element 27) for lenslet array or holographic or phase contrast methods including an intensity variation due to the phase of the particle. A spatial profile of the intensity I(x) may be measured as $$I(x)=1\pm 2\phi(x) \quad (14)$$

where $\phi(x)$ is the phase of the particle approximated as $$\varphi = \frac{2\pi}{\lambda}\Delta nd \quad (15)$$

In this method the intensities of the particles are recorded and a distribution of optical densities is obtained.

It is also possible to calibrate the cavity by using standard particles of know size, refractive index, and fluorescence properties. And, it is possible to use cavities with fixed, multiple steps in spacing to aid in calibration. This apparatus has the advantage that it can use a single image to simultaneously obtain a measurement of a reference feature, specimen optical density, and specimen size. The technique can also use machine vision and algorithms to create binary image maps to located spectral position, peak width, and intensity and can be performed quickly That method is resistant to clustering because the clusters can be directly imaged and can be differentiated from single particles.

An advantage of this embodiment is that multiple light sources using similar or different wavelengths and detectors at similar or different wavelengths can be employed to obtain simultaneous information on the optical properties in the image, including fringe displacement, phase, fluorescence, brightfield, darkfield, scatter, reflectance, transmittance, and the like. A further advantage is that there is no drift in the measurement as the zero correction is automatically included in image. Also the procedure can be done wet (flow or static fluid) or dry (higher contrast but in a dry state).

New mode of laser operation for small bioparticles using light fluctuation measurements There are three regimes of operation of the optical resonators as a laser, according to bioparticle size. In the geometrical limit where the particle radius a is much larger than the wavelength $\lambda$ of light, $a>>\lambda$ the laser is called a biocavity laser that exhibits multimode spectra that are useful for studying particle morphology, shape, and composition. In the intermediate Mie regime, where $a\approx\lambda$, the laser is called a nanolaser and exhibits a phenomenon of nano-squeezed light with single mode (both single longitudinal and single transverse mode) operation. In this mode, the spectra are simpler and useful for studying particle size and composition. In the Rayleigh limit where $a<<\lambda$ the bioparticles scatter light isotropically and do not support intracavity modes. Instead, the laser is used in a new way to measure laser cavity mode fluctuations arising from scattering from nanoparticles. These fluctuations can be used to study nanoparticle mass, shape, motion, and interactions with other particles and materials.

Particles larger than the wavelength of light produce the scattered field that peaks in the forward and near backward directions in contrast to smaller particles, which scatter light more uniformly. The angular width $\theta$ of the forward peak, is proportional to the ratio of the wavelength $\lambda$ to the particle's size $\theta\approx\lambda/a$. As the particle size decreases to the Mie regime, the scattering angle increases but is predominantly in the forward direction. As the particle size decreases further into the Rayleigh limit, the scattering angle becomes very large. Finite difference time domain calculations predict that the transition from Raleigh to Mie scattering occurs near bioparticle diameters near 200-300 nm.

In the geometrical and Mie lasing regimes, light cycles through the particle, cavity, and semiconductor gain region till a stable mode pattern is formed. Light scattered at small angles is reflected multiple times in the cavity and builds up stable lasing modes in the lasing process.

In this manner, bioparticles inside the laser cavity serve as optical waveguides to confine light generated in the resonator by the semiconductor. The waveguiding effect is due to slight differences in the dielectric constants between various cell components and the surrounding fluids. The laser operates at resonant frequencies established by the dielectric properties of the cells. By using a high resolution spectrometer or interferometer, these lasing frequencies can be resolved into narrow spectral peaks. In the Rayleigh limit, the particle behaves as a dipole and radiates in all directions. The large angle scatter light is lost sideways from the longitudinal cavity. The Rayleigh mechanism tends to scatter light at large angles relative to the incident beam. Thus, these tend to be loss mechanisms for operation of the laser which operates principally with light in the forward and backward directions.

Operation in the Mie Regime

Bioparticles with size near the wavelength of light fall into the Mie regime where nano-squeezed light (light squeezed in space) is present in the laser. The approximate condition for nano-squeezing at 850 nm for 100 nm spectral gain bandwidth gives a $\approx$500 nm. Thus, the condition for nano-squeezing is that the bioparticle must be approximately smaller than the wavelength of light. Operation of the laser in the Mie regime is useful for quantifying changes in biomolecular composition that contribute to the intrinsic refractive index.

Using nano-squeezed light conditions, the laser has recently been used to study biophotonic properties of genetically modified mitochondria of several hundred nm in size isolated from animal and yeast cells. Because the mitochondria are so tiny, it has been difficult to study them using standard light microscope or flow cytometry techniques. And, electron or atomic force microscopies are mostly limited to nonviable organelles so they cannot reproduce physiologic measurements. The nanolaser is an ultrasensitive method of detection for submicron particles that uses nano-squeezing of light into photon modes imposed by ultrasmall dimensions in a submicron laser cavity. This method can rapidly probe the morphology and biochemistry of an organelle in a near-physiologic state. Thus, nanolaser spectroscopy is an ideal tool for studying the physical and biochemical changes in bioparticles.

The studies show that stressed or diseased states of the organelles can be quantified by the nanolaser spectra. The data revealed large changes in the physical optics of yeast mitochondria induced by genetic manipulation. These features reflect new states of stressed or diseased cells that are caused by large depletions or changes in biomolecular composition that contribute to the intrinsic refractive index. Most of these biomolecules are proteins with metallic complexes intended for normal electron transport function. The altered index is a biophysical consequence of dramatic changes that occur in the biomolecular distribution and subcellular organization of healthy cells under stress, or in disease states that produce cellular dysfunction.

The nanolaser was successful in quantifying the biophysical statistics in this controlled experiment with genetic manipulation of the yeast mitochondria, and has been shown useful for studying other kinds of mitochondria.

Operation in the Rayleigh Limit

In the Rayleigh limit, $a \ll \lambda$ the particles scatter light over wide angles and do not support a longitudinal cavity mode. Instead, the particle and its motion produce a scattering loss and can randomly modulate a pre-existing laser mode defined by the cavity. The degree of modulation and its corresponding frequency spectrum will be dependent on the volume of the cavity mode, and the size, motion, and concentration of the particles. Larger particles will be expected to scatter more light and perturb the lasing mode more strongly. As the particle diameter decreases relative to the mode volume, the perturbation will decrease below a sensitivity limit defined by pre-existing noise in the mode volume. Sensitivity can be enhanced by operating a pre-existing cavity mode just above the lasing threshold condition. For example, intensity fluctuations can be recorded as a function of time or frequency to given information about the diffusional and rotational motion of bioparticles. This method has the advantage of being a non-destructive technique that can capture important information regarding size, motion, and dynamic interactions of the bioparticles with other bioparticles or material surfaces.

The light signal emitted from the cavity can be the direct beam of coherent light, coherent light scattered out the beam, or fluorescence from a fluorescent bioparticle. These methods have certain advantages over prior art methods of dynamic light scattering (DLS) and fluorescence correlation spectroscopy (FCS), and these two techniques are also adaptable to a resonant optical cavity and incorporated into the invention. FCS is a common technique to experimentally characterize fluorescent species (proteins, biomolecules, etc.) and their dynamics. Using confocal or two photon microscopy, light is focused on a sample and the measured fluorescence intensity fluctuations (due to diffusion, chemical reactions, aggregation, etc.) are analyzed using the temporal autocorrelation. FCS obtains quantitative information such as diffusion coefficients, hydrodynamic radii, and average concentrations kinetic chemical reaction rates. DLS is used to determine the size distribution profile of small particles in solution. Time-dependent fluctuations in the scattering intensity are due to small molecules in solutions undergoing Brownian motion and dynamically changing coherent interference. The intensity fluctuation contains information about movement of the scatterers. The dynamic information of the particles is derived from an autocorrelation function g given by $$g^2(q, \tau) = \frac{\langle I(t)I(t+\tau)\rangle}{\langle I\rangle^2}$$

where q is a wave vector, $\tau$ is a delay time, and I is the intensity.

Both of these techniques are useful for gaining insight into bioparticle dynamics. However, DLS is limited by requirements for high purity specimens, ultra-clean surfaces of the liquid cuvette, and typically requires a large scattering volume ~10-100 uL. Thus, the measurement in a large volume gives only averages over large numbers of vesicles. FCS can sample very small volumes ~1 fL and probe single molecules. Unfortunately, the small volume implies high laser irradiance and consequent bleaching of the fluorescent probe molecules, limiting the FCS method.

The invention solves these technical difficulties by using coherent light fluctuations from intracavity scattering losses and absorption induced by the bioparticles. Either fluctuations in the coherent emitted beam or fluctuations in the coherent scattered light may be used. The dynamic motion of bioparticles can be studied by placing them into resonant optical cavities with micron and submicron dimensions formed with dielectric and/or semiconductor materials that have been surface-functionalized (e.g. polyethylene glycol) for optimal chemical, mechanical, and optical properties. The small lateral dimension and the standing wave electromagnetic field in the cavity creates a much smaller optical interaction volume than prior art, enhancing sensitivity. The cavities may take the form of a micro-titer plate (microcavity wells) with a static fluid or a microchannel cavity for flowing fluids.

The laser fluctuations can also be used to measure bioparticle motion in whole cells in the cavity. The fluctuations are sensitive to scattering from the distribution and motion of protein molecules and organelles in the cell. The method has the potential to probe intra-molecular polarization, molecular weight, shape and folding configuration structure since the coherent spectral linewidth is the Fourier transform of the time-correlated intensity fluctuations induced by molecular structure and motion.

None of the prior art on biological microcavity lasers teaches limitations to laser operation with small bioparticles. It doesn't teach the ultimate limits on bioparticle size to prevent laser operation. It doesn't teach limiting values on the particle refractive index, mismatch of index with carrier fluid, or particle size that would prevent the laser from working. Thus, prior art doesn't teach how the laser must be operated in a radically new way to measure very small bioparticles.

The ultimate limits of detectability for various bioparticles using optical techniques are influenced by light scattering. The total scattering cross section $\sigma_T$ of a single bioparticle scales as $((n^2-1)/(n^2+2))$ where $n=n_2/n_1$ is the ratio of the refractive index of the bioparticle to that of the surrounding media. For large values of n>10 (metallic behavior) this factor approaches a limiting value of 1. For small index differences $\delta=(n_2-n_1)/n$ the factor has the limiting form $4\delta^2/9$. The cross section also depends on the parameter $q=2\pi a/\lambda$ where a is the particle radius and $\lambda$ the wavelength of light. At small q<<1, the cross section increases as $q^4$. At intermediate q>0.1 the dependence is stronger approximately $\sim q^6$ in this case. For $q\approx 0.5$, the dependence becomes linear as q, and $\sigma_T$ becomes maximum at $q\approx 1$. For higher values of q, $\sigma_T$ exhibits damped oscillation and approaches twice the classical value of the cross section $\sigma=2\pi a^2$.

FIG. 10*a* shows a laser with a gain region 32, a resonant cavity 28 to confine light and select coherent light wavelengths, a means to extract light from the cavity. In the laser, a semiconductor provides the light, gain, and one reflective side of the cavity, and the glass chip completes the cavity and provides a partially transmissive mirror to leak light to the outside. The normal lasing process works as follows. The semiconductor wafer is energized externally with a separate pump laser or electrical pump to control spatial location and magnitude of the gain. The pump generates spontaneous (incoherent) light from a thin quantum-electronic layer in the semiconductor. In this condition below lasing threshold, the laser emits only incoherent, weak, spectrally broad light. As the pump power input is increased, a threshold is exceeded and the laser is triggered and the output power increases rapidly.

FIG. 10*b* shows a power output versus power input curve, showing that the light grows very rapidly (about 100-fold) and exhibits a highly nonlinear amplifying region. In this nonlinear region, a small change in the cavity can produce a large change in the output power. When bioparticles are present, they introduce scattering losses and phase change and effectively increase the threshold condition for lasing.

When the laser cavity length is the order of the wavelength of light, the laser operates on a single longitudinal and single transverse mode (single frequency). The cavity length can be shortened more to give a small number of field antinodes 60 (as shown in FIG. 10*a*) or single antinode to reduce the laser mode volume. The lateral mode dimension is reduced by fabricating a small lateral gain region or using a post waveguide or the like or using current confinement such as oxide confinement or ion implantation (electrical pump) or small pump spot or nonlinear (multiphoton) optical pumping.

When the mode volume is very small, the effect of individual bioparticles is more pronounced. The number of bioparticles in the lasing volume obeys Poisson statistics given by Eq. 5. The fluctuating number of bioparticles (64, FIG. 10*a*) in the mode volume is driven by Brownian motion and results in fluctuations in the lasing threshold condition. These fluctuations result in power output fluctuations (FIG. 11*b*) that can be compiled into histograms as in FIG. 11*a* or correlated in time to give correlation curves as shown in FIG. 11*c*. The laser signal can be self-correlated or cross-correlated with the pump source or light from another reference region in the laser. The shape of the correlation spectra gives information about the particle size and possible distribution of sizes.

Intracavity correlation spectroscopy can also be used to measure laser linewidth fluctuations arising from nanoparticles in the lasing mode volume. The coherent spectral linewidth is a measure of spatial correlation through a structure factor. For a laser microcavity of length L loaded with scattering centers having total scattering cross section $\sigma_T$ and average density $\rho$, the lasing linewidth $\delta\lambda$ in the high scatter limit is estimated by $\delta\lambda\approx(2/\pi)(K/P)(\rho L\sigma_T)^2$ where K is a linewidth enhancement factor, and P is the photon emission rate. Thus, the laser linewidth is sensitive to the scattering of light by bioparticles by a second order dependence on the scattering cross section. Increased scattering by correlation of bioparticles or interaction with other bioparticles will be evident by broadened lasing linewidth. In the event that chemical reactions occur between bioparticle species, the bioparticle can increase in size and change refractive index thus changing the scattering cross section and linewidth. The changes arising from interactions with multiple bioparticle species can be referenced to measurements on solutions with single species of bioparticles.

In the laser cavity a periodic electromagnetic field is set up in a standing wave. The field intensities at the antinodes are much higher (~100 times or more) than the external field intensity, giving larger scattering intensity. For small bioparticles undergoing Brownian motion, there will exist a 3-dimensional velocity distribution that interacts with the longitudinal periodic field. Scattering of light will occur only near the antinodes of the field, making the scattering volume smaller than the physical volume of the laser cavity mode. In addition, the field will exert optical-field gradient forces on the bioparticles. The force is a function of the intracavity field strength, bioparticle size and shape, polarizability, relative refractive indices of the fluid and bioparticle (dependent in turn on the molecular (e.g. chromophore) content in the bulk and surface or membrane). As a result, the bioparticles with lower velocities will tend to be confined in 2-dimensional oblate ellipsoids established by the longitudinal standing wave. This will tend to enhance the interaction within the longitudinal mode. As the intracavity field intensity is reduced, the bioparticles will exhibit more 3-dimensional motion. The differences between 2- and 3-dimensional motion will depend upon the detailed shape of the vesicles.

The dynamical interaction of the bioparticles within the cavity can be examined by varying the laser pump power, effects of internal or external optical trapping, light input versus light curves (threshold, maximum slope, and saturation level). Also, the bioparticles will be polarized by the electromagnetic field in the cavity. The polarization of the bioparticle will depend upon the frequency, shape, and polarizability. The polarization will influence the electromagnetic force exerted by the field on the bioparticle. Bioparticles with different shapes, such as rods or spheres, will exhibit different motion.

The bioparticles act as driven masses in a viscous medium and exhibit resonance motion under certain conditions. By changing the intracavity power, viscosity, electromagnetic field distribution, these conditions can be changed to drive the bioparticles into and out of resonance and determine their physical properties. The pump laser pulse frequency, pump laser pulse width (femtosecond, nanosecond, or continuous-wave) can be used to modulate the interaction of the field with the bioparticles to control and measure dynamical motion.

Multiple or arrays of lasing elements can be formed by defining waveguiding or gain guiding regions (32 with 70) as shown in FIG. 12. Such arrays can operate with independent elements or coupled lasers by changing their spacing. The array can serve to detect and analyze local interactions over a larger volume of bioparticles or generate a stronger signal. Further, the array antinodes 60 can serve to selectively trap bioparticles by controlling the pump power, frequency, or pump pulse duration. Simultaneously, the emitted light signals can provide information about the type of bioparticle held in the trap. Some bioparticles will respond to higher frequencies and will be trapped while others are not. Using controlled fluid flow, the untrapped bioparticles may be separated from the trapped bioparticles.

Finally, FIG. 13 shows how the array of light sources 80, operated as intracavity or extracavity lasers or spontaneous emitters, can be integrated with a reflector/detector array 84. Protective, biocompatible overlayers 82 are used to contact and enclose one or more living cells 86 in tissue culture. The nanolaser array is powered electrically or optically by a power interface 88. The lasers can be powered collectively or synchronized in time with the detector to isolate each locality. The output light output through a reflector to a detector array 84 to sense individual laser output intensities. The whole assembly acts as a self-contained biological probe system that eliminates the need for a microscope and associated optics. The system can be used to probe intracellular molecular activity, intercellular cell signaling, or extracellular molecular activity. These methods represent advantageous new ways to perform analyses of bioparticles and have wide ranging application for basic cell biology, cell culture, detection of disease, pathology, genetic engineering, environmental screening of toxins, pharmaceuticals, agricultural, and fermentation processes, biofuel production, and the like.

What is claimed is:

1. A method for analyzing a bioparticle, or plurality of bioparticles, in a micro/nano-optical resonator comprising the steps of:
   a. establishing optical resonance in the optical resonator;
   b. measuring optical resonance of the resonator in the absence of a bioparticle;
   c. measuring optical resonance in the presence of a bioparticle;
   d. using the changes in optical resonance to determine optical properties of a bioparticle; and
   e. relating the optical properties to biomolecular composition of the bioparticle, whereby information about the bioparticle is obtained and is transformed to an output display using the benefits of light as non-contacting, fast, and noninvasive and without use of molecular tags, and
whereby statistical information about a population of bioparticles is quickly obtained to assess their material condition, and
whereby information about the state of health or disease, or normalcy or abnormalcy, of the bioparticle is obtained, and
whereby changes in biomolecular composition occurring in normal, stressed or diseased cells is assessed by measuring the distribution of optical properties in a population of bioparticles.

2. The method of claim 1 using a resonator with an activated gain region with a biocompatible protective layer so the combination acts as a laser that is triggered on by the presence of a bioparticle.

3. The method of claim 1 using a measurement of a detuning of a resonance in a spectrum or detuning across space in the resonator.

4. The method of claim 1 using a measurement of a detuning in an optical resonator in combination with measurement of phase contrast, diffraction, scattering, fluorescence, reflectance, transmittance, and/or absorption.

5. The method of claim 1 using a measured optical parameter to provide information about the size, refractive index or polarizability, and/or biomolecular composition of a bioparticle, or plurality of bioparticles.

6. The method of claim 1 providing a means for calibrating the measurements, including a zero and scale factor, and for making corrections to these factors arising from changes in time during the measurement procedure.

7. The method of claim 1 providing a means for moving bioparticles through inlet and outlet ports to reservoirs, greatly larger than the bioparticles, and interconnected by narrow channels to entrain flowing bioparticles essentially one by one through regions of the resonator.

8. The method of claim 1 where the bioparticle, or plurality of bioparticles, is applied to a component of the resonator, either in a wet or dry condition, and the component assembled with other components to form the resonator.

9. The method of claim 1 where the bioparticle is a biological cell, mitochondrion or organelle, chloroplast or other plastid, or a nonbiological particle.

10. A method for analyzing the state of health of a bioparticle, or plurality of bioparticles, comprising the steps of:
    a. isolating the bioparticle from a cell;
    b. measuring the optical properties of the bioparticle in an optical resonators;
    c. collecting the measured optical properties into a histogram or statistical distribution;
    d. calibrating the distribution by providing a zero and scale factor or using a known distribution from a reference specimen;
    e. correcting the distribution for a drift or change in time, if necessary;
    f. determining statistical properties including mean, standard deviation, and variance by direct computation or fitting the measured distribution with known mathematical distribution functions, including analysis for multiple components or heterogeneous distributions; and
    g. comparing the measured distribution with distributions from normal bioparticles, whereby statistical information about the state of health or disease, or normalcy or abnormalcy, of a population of bioparticles is obtained and is transformed to an output display.

11. A method for analyzing the state of health of a bioparticle, or plurality of bioparticles, in an optical resonator comprising the steps of:
    a. providing a means for recording images and resonance detuning by a bioparticle;
    b. using digital imaging processing, including binary and/or grey level computation, to analyze images for detuning changes in the resonator when a bioparticle is present;
    c. determining particle size, position, width, height, and detuning measurement for collection into histograms, statistical tables or graphs, or image correlations for further analysis;
    d. analyzing said histograms, tables, graph, or correlations to determine mean, standard deviation, and variance of image properties;
    e. determining statistics of biophysical properties of bioparticles including mean, standard deviation, and variance by direct computation or fitting the measured distribution with known mathematical distribution functions, including analysis for multiple components or heterogeneous distributions; and
    f. comparing the measured distribution with distributions from normal bioparticles, whereby statistical information about the state of health or disease, or normalcy or abnormalcy, of a population of bioparticles is quickly obtained using imaging for both size and composition and is transformed to an output display.

* * * * *